United States Patent
Del Nido et al.

(10) Patent No.: US 10,420,645 B2
(45) Date of Patent: Sep. 24, 2019

(54) RIGHT VENTRICULAR PAPILLARY APPROXIMATION

(71) Applicants: Children's Medical Center Corporation, Boston, MA (US); The Brigham and Women's Hospital, Inc., Boston, MA (US)

(72) Inventors: Pedro J. Del Nido, Lexington, MA (US); Haruo Yamauchi, Tokyo (JP); Nikolay V. Vasilyev, Belmont, MA (US); Maria Jose M. Nunes Pereira, Cambridge, MA (US); Eoin D. O'Cearbhaill, Cambridge, MA (US)

(73) Assignees: Children's Medical Center Corporation, Boston, MA (US); The Brigham and Women's Hospital, Inc., Boston, MA (US)

( * ) Notice: Subject to any disclaimer, the term of this patent is extended or adjusted under 35 U.S.C. 154(b) by 1024 days.

(21) Appl. No.: 14/377,560

(22) PCT Filed: Feb. 15, 2013

(86) PCT No.: PCT/US2013/026428
§ 371 (c)(1),
(2) Date: Aug. 8, 2014

(87) PCT Pub. No.: WO2013/123388
PCT Pub. Date: Aug. 22, 2013

(65) Prior Publication Data
US 2015/0025553 A1    Jan. 22, 2015

Related U.S. Application Data

(60) Provisional application No. 61/598,966, filed on Feb. 15, 2012.

(51) Int. Cl.
*A61F 2/24* (2006.01)
*A61B 17/04* (2006.01)
(Continued)

(52) U.S. Cl.
CPC ........ *A61F 2/2487* (2013.01); *A61B 17/0401* (2013.01); *A61B 2017/00243* (2013.01);
(Continued)

(58) Field of Classification Search
CPC .... A61F 2/2487; A61F 2/2481; A61F 2/2478; A61B 17/08; A61B 17/0643;
(Continued)

(56) References Cited

U.S. PATENT DOCUMENTS

| 4,836,204 A | 6/1989 | Landymore et al. |
| 550,948 A | 4/1996 | Dunlop |

(Continued)

FOREIGN PATENT DOCUMENTS

WO    WO 02/087481    11/2002

OTHER PUBLICATIONS

Supplemental European Search Report; EP 13 74 8874; dated Sep. 8, 2015; C. Maier; 6pp.
(Continued)

*Primary Examiner* — Christopher L Templeton
*Assistant Examiner* — Chima U Igboko
(74) *Attorney, Agent, or Firm* — Fish & Richardson P.C.

(57) ABSTRACT

A device for treating tricuspid regurgitation includes a shaft and a first fixation mechanism disposed on a distal end of the shaft. The first fixation mechanism is configured to anchor the device to a first cardiac tissue. The device includes a second fixation mechanism disposed on a proximal end of the shaft. The second fixation mechanism is configured to anchor the device to a second cardiac tissue. The device includes an approximation mechanism connecting the first
(Continued)

fixation mechanism and the second fixation mechanism, wherein the approximation mechanism causes the second fixation mechanism to move along the shaft toward the first fixation mechanism to approximate the first cardiac tissue and the second cardiac tissue.

14 Claims, 25 Drawing Sheets

(51) Int. Cl.
  *A61M 25/04* (2006.01)
  *A61M 25/02* (2006.01)
  *A61B 17/00* (2006.01)
  *A61B 17/08* (2006.01)

(52) U.S. Cl.
  CPC .......... *A61B 2017/00407* (2013.01); *A61B 2017/00606* (2013.01); *A61B 2017/0406* (2013.01); *A61B 2017/0409* (2013.01); *A61B 2017/0419* (2013.01); *A61B 2017/0451* (2013.01); *A61B 2017/0464* (2013.01); *A61B 2017/081* (2013.01); *A61M 25/04* (2013.01); *A61M 2025/0233* (2013.01)

(58) Field of Classification Search
  CPC ...... A61B 17/0487; A61B 2017/06014; A61B 2017/081; A61B 2017/086; A61B 2017/088; A61B 2017/0496; A61B 2017/0488; A61B 2017/049; A61B 2017/0429; A61B 2017/043; A61B 2017/0432; A61B 2017/0433; A61B 2017/0435; A61B 2017/0437; A61B 2017/1103
  See application file for complete search history.

(56) References Cited

U.S. PATENT DOCUMENTS

| | | | |
|---|---|---|---|
| 5,855,614 | A | 1/1999 | Stevens et al. |
| 7,037,334 | B1 | 5/2006 | Hlavka et al. |
| 7,077,862 | B2 | 7/2006 | Vidlund et al. |
| 7,087,064 | B1 | 8/2006 | Hyde |
| 7,189,199 | B2 | 3/2007 | McCarthy et al. |
| 7,335,213 | B1 * | 2/2008 | Hyde ................ A61B 17/0469 606/151 |
| 7,704,269 | B2 | 4/2010 | St. Goar et al. |
| 2002/0115994 | A1 | 8/2002 | Teirstein et al. |
| 2004/0122456 | A1 | 6/2004 | Saadat et al. |
| 2005/0251208 | A1 | 11/2005 | Elmer et al. |
| 2006/0229708 | A1 | 10/2006 | Powell et al. |
| 2007/0118151 | A1 | 5/2007 | Davidson |
| 2008/0294251 | A1 * | 11/2008 | Annest ............... A61B 17/0401 623/3.1 |
| 2009/0030411 | A1 | 1/2009 | Werneth et al. |
| 2009/0082619 | A1 | 3/2009 | De Marchena |
| 2009/0177266 | A1 | 7/2009 | Powell et al. |
| 2009/0306681 | A1 | 12/2009 | Del Nido et al. |

OTHER PUBLICATIONS

Office Action in European Application No. 13748874.8, dated Feb. 3, 2017, 5 pages.
International Preliminary Report on Patentability issued in PCT/US2013/026428 dated Aug. 28, 2014 (8 pages).
International Search Report and Written Opinion issued in PCT/US2013/026428 dated Jun. 21, 2013 (12 pages).
Mishra et al., "Coapsys mitral annuloplasty for chronic functional ischemic mitral regurgitation: 1-year results," Ann. Thorac. Surg., 81:42-46 (2006).
Yang et al., "Using contracting band to improve right ventricle ejection fraction for patients with repaired tetralogy of Fallot: a modeling study using patient-specific CMR-based 2-layer anisotropic models of human right and left ventricles," J. Thorac. Cardiovasc. Surg., 145:285-293 (2013).
European Office Action in Application No. 13748874.8, dated Oct. 24, 2017, 5 pages.

* cited by examiner

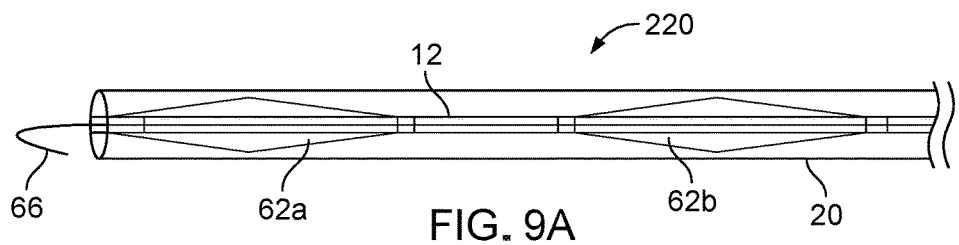
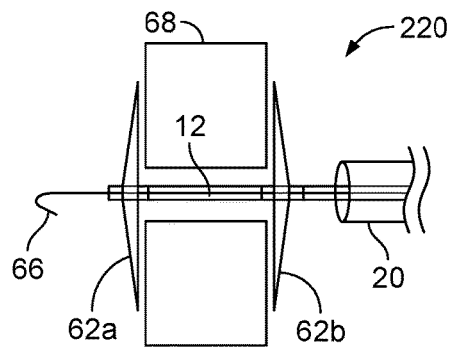
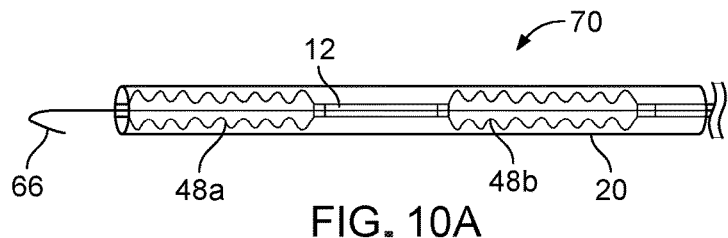
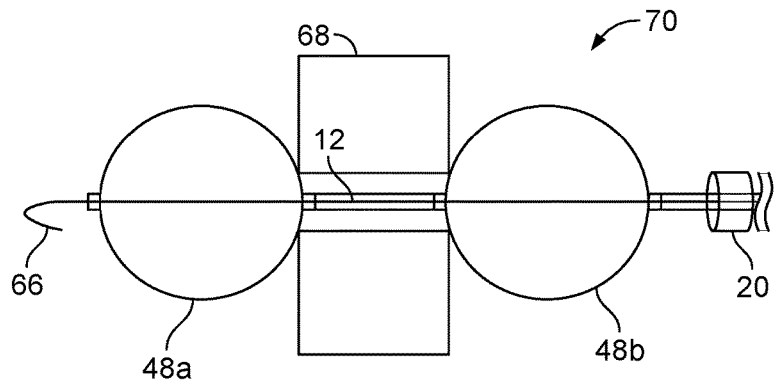

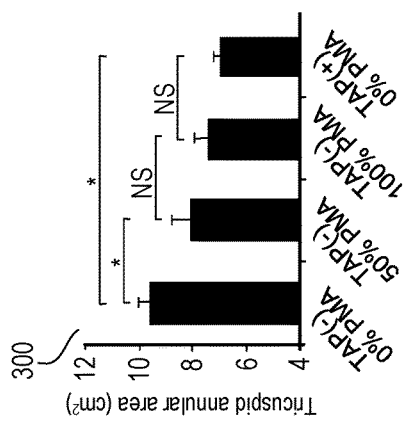
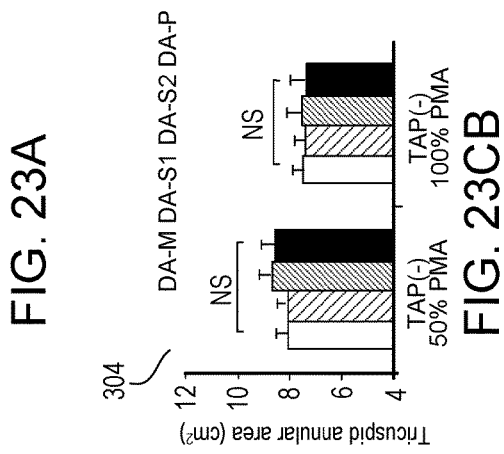

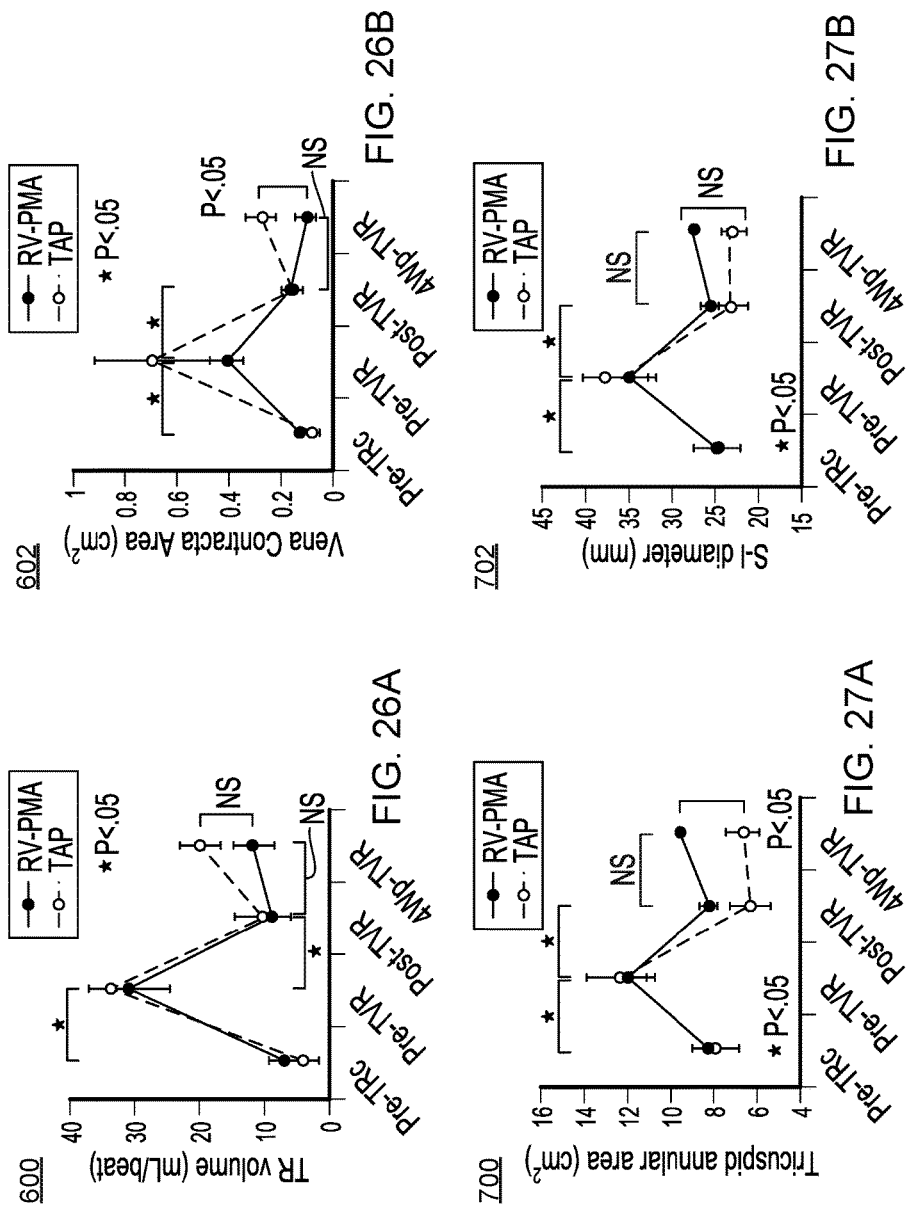

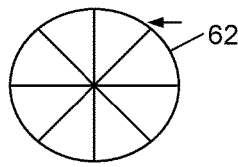
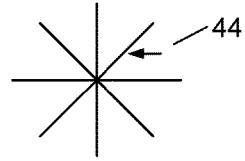
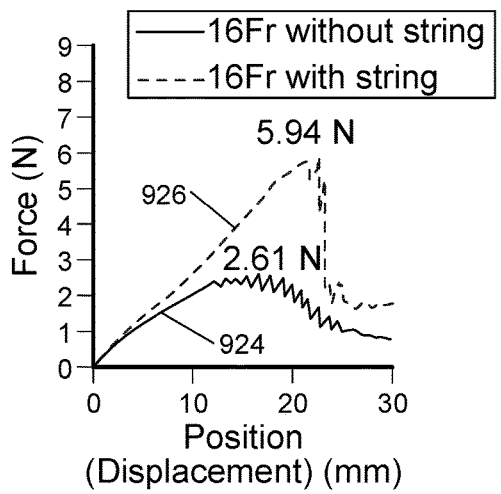
FIG. 31A
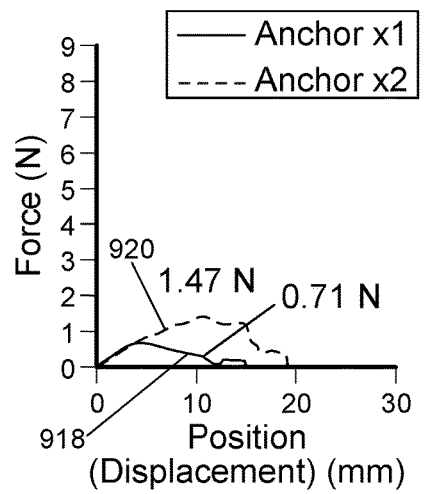
FIG. 31B
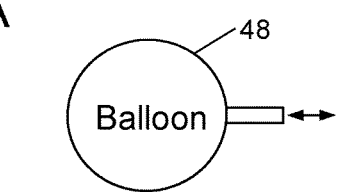
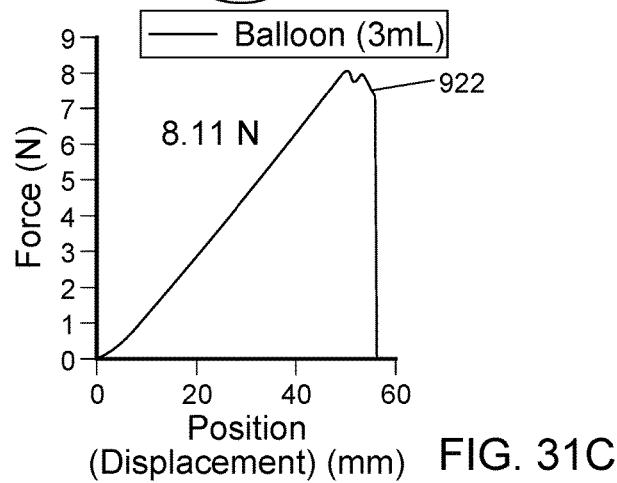
FIG. 31C

RIGHT VENTRICULAR PAPILLARY APPROXIMATION

CROSS REFERENCE TO RELATED APPLICATIONS

This application claims priority from U.S. Provisional Application Ser. No. 61/598,966, filed on Feb. 15, 2012, the contents of which are incorporated herein by reference in their entirety.

STATEMENT AS TO FEDERALLY SPONSORED RESEARCH

This invention was made with Government support under Grant No. HL073647 awarded by the National Institutes of Health. The Government has certain rights in the invention.

FIELD OF THE INVENTION

The invention relates to devices and methods for right ventricular papillary approximation.

BACKGROUND OF THE INVENTION

Tricuspid regurgitation (TR) adversely affects cardiac mortality in a number of clinical settings. In adults, "functional" TR from tricuspid annular dilation and right ventricular enlargement is a common TR mechanism and can be secondary to left-sided valve and ventricular dysfunction or pulmonary hypertension. Tricuspid annuloplasty (TAP) can be used to repair the tricuspid valve in cases of functional TR. Functional TR also occurs in children, but TAP is often not appropriate, because the treatment may impede the growth potential of the tricuspid annulus. The mechanism of regurgitation in functional TR and in children with some forms of congenital TR is thought to be tethering of the leaflets from outward displacement of papillary muscles in the dilated right ventricle, which often cannot be effectively treated by annuloplasty.

SUMMARY OF THE INVENTION

The disclosure is based, at least in part, on the discovery that, to treat tricuspid regurgitation, the tricuspid annular dimension and the geometry of the right ventricle can be changed, for instance, by drawing together sections of cardiac tissue (i.e., approximating the tissues). Devices for right ventricular papillary approximation include fixation mechanisms, such as hooks, anchors, or other types of fixation mechanisms, on both the distal end and the proximal end of a shaft. The fixation mechanisms can be anchored to cardiac tissue and drawn together, causing the cardiac tissue to which they are anchored to be drawn together as well. The device can be used in treatments to reduce or eliminate tricuspid regurgitation. For instance, the fixation mechanisms can be anchored to the ventricular septum and the anterior papillary muscle or right ventricular free wall, such that these tissues are brought into close proximity or contact when the fixation devices are drawn together.

In a general aspect, a device for treating tricuspid regurgitation includes a shaft and a first fixation mechanism disposed on a distal end of the shaft. The first fixation mechanism is configured to anchor the device to a first cardiac tissue. The device includes a second fixation mechanism disposed on a proximal end of the shaft. The second fixation mechanism is configured to anchor the device to a second cardiac tissue. The device includes an approximation mechanism connecting the first fixation mechanism and the second fixation mechanism, wherein the approximation mechanism causes the second fixation mechanism to move along the shaft toward the first fixation mechanism to approximate the first cardiac tissue and the second cardiac tissue.

Embodiments may include one or more of the following.

The first fixation mechanism includes at least one of the following: a hook, an anchor, an umbrella, and a balloon. The second fixation mechanism includes at least one of the following: a hook, an anchor, an umbrella, and a balloon.

The approximation mechanism includes at least one of a string, a wire, and a thread.

The device includes a locking mechanism to lock the device in a configuration that causes the first cardiac tissue and the second cardiac tissue to be approximated together. In some cases, the locking mechanism includes at least one of a ratchet and a screw locking mechanism.

In a folded configuration, the first and second fixation mechanisms are collapsed to be substantially parallel to the shaft, and in a deployed configuration, the first and second fixation mechanisms are expanded outward from the sheath in a second configuration.

The device includes a sheath configured to contain the shaft. The first and second fixation mechanism are collapsed to be substantially parallel to the shaft when the shaft is contained within the sheath.

The first cardiac tissue is at least one of papillary muscle and right ventricular free wall, and the second cardiac tissue is ventricular septal tissue.

The shaft includes an actuator.

In a general aspect, a method for treating tricuspid regurgitation includes anchoring a first fixation mechanism disposed at a distal end of a shaft to a papillary muscle and anchoring a second fixation mechanism disposed at a proximal end of the shaft to a ventricular septal tissue. The method includes moving the second fixation mechanism along the shaft toward the first fixation mechanism. Moving the second fixation mechanism causes the papillary muscle or a right ventricular free wall and the ventricular septal tissue to be approximated together to treat the tricuspid regurgitation.

Embodiments may include one or more of the following.

Anchoring the first fixation mechanism includes removing the distal end of the shaft from a sheath; and causing the first fixation mechanism to expand. Anchoring the second fixation mechanism includes removing the proximal end of the shaft from a sheath; and causing the second fixation mechanism to expand.

The first tissue and the second tissue are two sides of a first cardiac tissue. The method includes anchoring a third fixation mechanism disposed at a distal end of a second shaft to a first side of a second cardiac tissue; anchoring a fourth fixation mechanism disposed at a proximal end of the second shaft to a second side of the second cardiac tissue; and causing the first cardiac tissue and the second cardiac tissue to be approximated together.

In a general aspect, an assembly for treating tricuspid regurgitation includes a plurality of devices. Each device includes a shaft and a first fixation mechanism disposed on a distal end of the shaft. The first fixation mechanism is configured to anchor the device to a first cardiac tissue. Each device includes a second fixation mechanism disposed on a proximal end of the shaft. The second fixation mechanism is configured to anchor the device to a second cardiac tissue. Each device includes an approximation mechanism connecting the first fixation mechanism and the second fixation mechanism. The approximation mechanism causes the second fixation mechanism to move along the shaft toward the first fixation mechanism to approximate the first cardiac tissue and the second cardiac tissue. The assembly includes one or more connectors, each connector connecting a first device to at least one other device. The one or more connectors are operable to cause the first device to move closer to the at least one other device.

Embodiments may include one or more of the following.

The one or more connectors include at least one of strings, wires, and threads.

Each device further comprises a device locking mechanism to lock the device in a configuration that causes the first cardiac tissue and the second cardiac tissue to be approximated together. In some cases, the assembly includes at least one assembly locking mechanism configured to lock the position of each first device relative to each other device to which the first device is connected.

The shaft of at least one of the plurality of devices includes an actuator.

At least one of the connectors includes an actuator.

The devices and methods for right ventricular papillary approximation described herein have a number of advantages. The treatment of tricuspid regurgitation with right ventricular papillary approximation can alleviate functional tricuspid regurgitation by reducing annular dimension, right ventricular sphericity index, and valve tethering. Furthermore, the flexibility of the right ventricular papillary approximation approach (e.g., the adjustability of the three-dimensional positioning of the devices) allows for tricuspid valve repair that can be customized to each individual patient's unique anatomy. In addition, the approaches described herein can reduce or eliminate compression of the ventricular wall from the outside, thus limiting its interference with ventricular function.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIGS. 9A and 9B are diagrams of a device including an umbrella fixation mechanism in a collapsed state and a deployed state, respectively.

FIGS. 10A and 10B are diagrams of a device including a balloon fixation mechanism in a folded state and a deployed state, respectively.

FIGS. 23A and 23B are graphs of tricuspid annular area and the septal-lateral dimension of the tricuspid annulus, respectively, versus tricuspid annuloplasty for various extents of right ventricular papillary approximation.

FIGS. 23C and 23D are graphs of tricuspid annular area and the septal-lateral dimension of the tricuspid annulus, respectively, with tricuspid annuloplasty and various extents of right ventricular papillary approximation.

FIGS. 26A and 26B are graphs of tricuspid regurgitation volume and Vena Contracta area, respectively, versus time.

FIGS. 27A and 27B are graphs of tricuspid annular area and septal-lateral diameter, respectively, versus time.

FIGS. 31A-31C are graphs of the force tolerance of umbrella tips, anchors, and balloons.

DETAILED DESCRIPTION

To treat tricuspid regurgitation, the tricuspid annular dimension and the geometry of the right ventricle can be changed, for instance, by drawing together sections of cardiac tissue (i.e., approximating the tissues). Devices for right ventricular papillary approximation include fixation mechanisms, such as hooks, anchors, or other types of fixation mechanisms, on both the distal end and the proximal end of a shaft. The fixation mechanisms can be anchored to cardiac tissue and drawn together, causing the cardiac tissue to which they are anchored to be drawn together as well. The devices can be used in treatments to reduce or eliminate tricuspid regurgitation. For instance, the fixation mechanisms can be anchored to the ventricular septum and the anterior papillary muscle or right ventricular free wall, such that these tissues are brought into close proximity or contact when the fixation devices are drawn together.

Right Ventricular Papillary Approximation with a Single Device

Figure 1A:
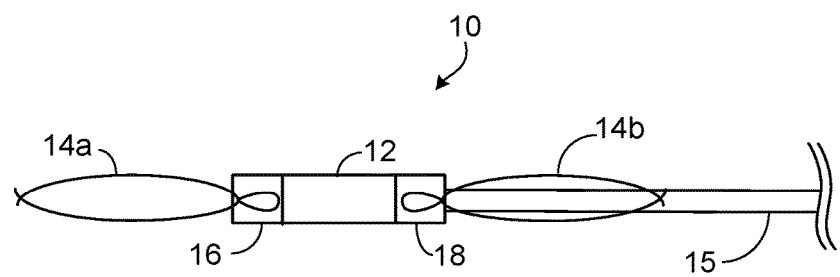
FIGS. 1A and 1B are diagrams of a device for right ventricular papillary muscle approximation in a folded state and a deployed state, respectively.
Figure 1B:
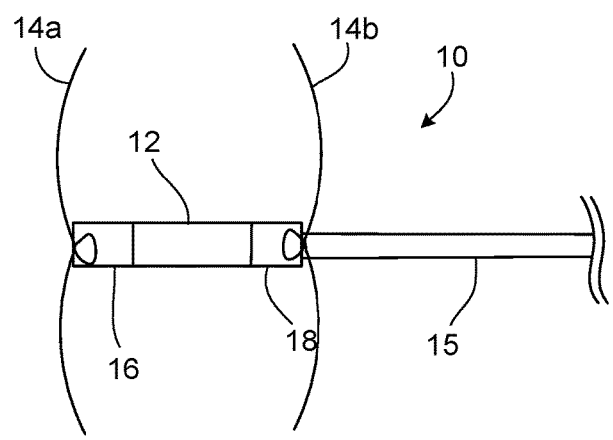

Referring to FIGS. 1A and 1B, a device 10 for right ventricular papillary muscle approximation includes a shaft 12 having a distal end 16 and a proximal end 18. Distal and proximal fixation mechanisms 14a, 14b, respectively, are positioned at the distal and proximal ends 16, 18 of the device 10. The fixation mechanisms 14a, 14b can be, e.g., hooks, anchors, discs, balloons, umbrellas, or other types of fixation mechanisms. The device 10 can be deployed in the heart to draw different portions of cardiac tissue together, thus reducing or eliminating tricuspid regurgitation. In particular, the fixation mechanism 14a, 14b can be expanded upon deployment of the device 10 to anchor the device to cardiac tissue. Once deployed, the fixation mechanisms 14a, 14b can be drawn together with an approximating mechanism 15, such as a string or a wire, causing the cardiac tissue to which the device 10 is anchored to be drawn together. For instance, to treat tricuspid regurgitation, the distal fixation mechanism 14a can be deployed onto the ventricular septum and the proximal fixation mechanism 14b can be deployed on the papillary muscle of the heart. Drawing the fixation mechanisms 14a, 14b together causes approximation of the ventricular septum and the papillary muscle or the right ventricular free wall.

Figure 2A:
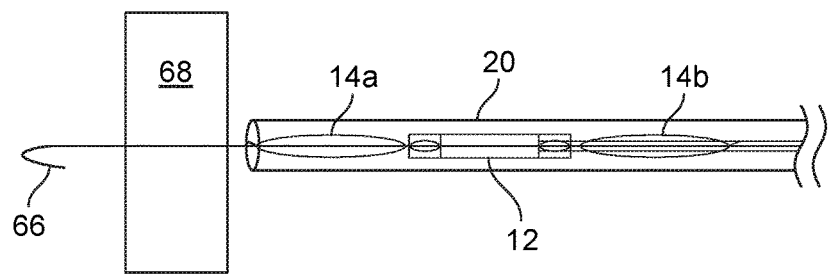
FIGS. 2A-2D are diagrams of an approach for deploying a device in the heart.
Figure 2B:
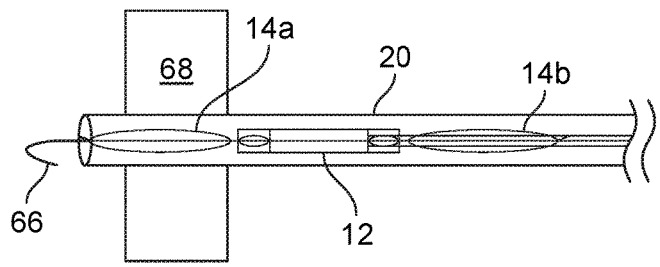
Figure 2C:
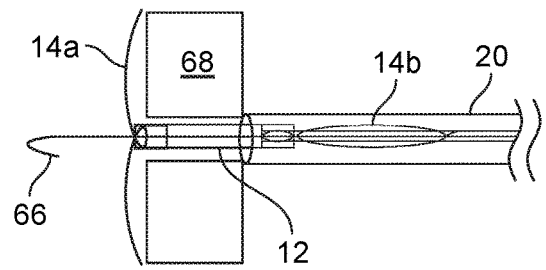
Figure 2D:
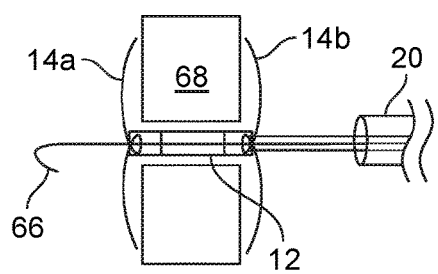

Referring to FIGS. 2A-2D, to deploy the device 10 into the heart for right ventricular papillary muscle approximation, the device 10 is folded into a sheath 20. The sheath 20 is approached to the heart by a catheter, a needle, or another mechanism, and a guide wire 66 penetrates cardiac tissue 68, such as a septal wall or a papillary muscle (FIG. 2A). The sheath 20 penetrates the cardiac tissue 68 guided by the guide wire 66 (FIG. 2B). The distal end 16 of the device 10 is deployed by pushing the device 10 at least partially out of the sheath 20 (FIG. 2C). Upon deployment of the device, the distal fixation mechanism 14a unfolds into an open position. The proximal end 18 of the device is then deployed, causing the proximal fixation mechanism 14b to unfold into an open position (FIG. 2D). In its deployed configuration, the device 10 is fixed at the puncture side of the cardiac tissue 68. In the illustrated example, the distal and proximal fixation mechanisms 14a, 14b anchor to the same portion of cardiac tissue 68. In some examples, e.g., to treat tricuspid regurgitation, the distal fixation mechanism 14a can anchor to a first type of cardiac tissue, such as the septal wall, and the proximal fixation mechanism 14b can anchor to a second type of cardiac tissue, such as the papillary muscle. When the distal and proximal fixation mechanisms 14a, 14b are drawn together, the septal wall and the papillary muscle or the right ventricular free wall can be drawn together.

Figure 3A:
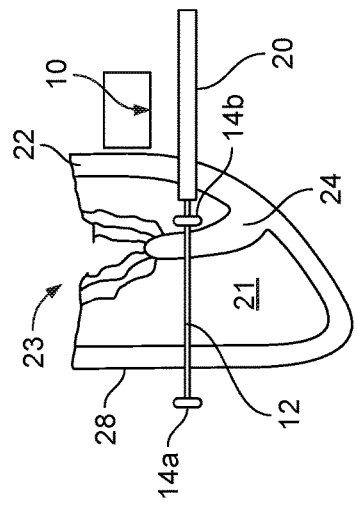
FIGS. 3A-3D are diagrams of an approach for deploying a device in the heart.
Figure 3B:
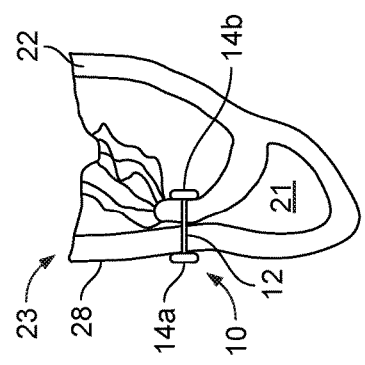
Figure 3C:
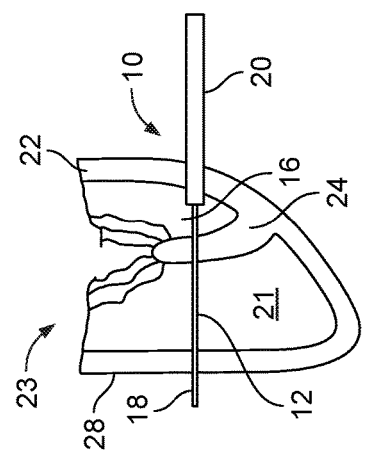
Figure 3D:
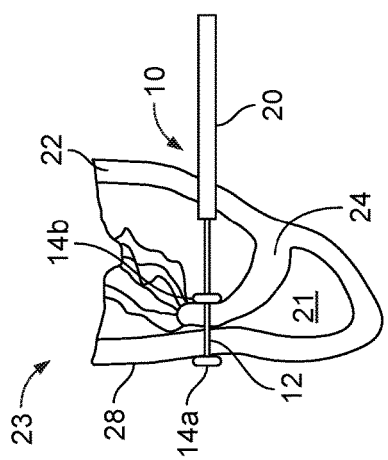

Referring to FIGS. 3A-3D, in an example approach to deploying the device 10, the device 10 can be inserted into a right ventricle 21 of a heart 23 from the epicardial surface of the right ventricle. A sheath 20 containing the device 10 is introduced into the right ventricle 21 through a right ventricle free wall 22. The shaft 12 of the device 10 is advanced from the sheath 20 to penetrate the anterior papillary muscle 24 and further advanced toward a ventricular septum 28. The shaft 12 may penetrate the anterior papillary muscle 24 at a middle portion of the papillary muscle (as shown in the illustrated embodiment), at a head portion of the papillary muscle, or at a base portion of the papillary muscle. The shaft 12 penetrates the ventricular septum 28 (FIG. 3A). The distal fixation mechanism 14a is deployed at the distal end 16 of the shaft 12 in the left ventricle and anchors to the ventricular septum 28. The proximal fixation mechanism 14b is deployed between the anterior papillary muscle 24 and the right ventricle free wall 22 toward the proximal end 18 of the shaft 12 (FIG. 3B). The distance between the fixation mechanisms 14a, 14b is shortened by approximating the fixation mechanisms 14a, 14b with an approximating mechanism 15 such as a string, a wire, a thread, or another type of approximating mechanism, such that the anterior papillary muscle 24 and the ventricular septum 28 come into close proximity or contact with each other (FIG. 3C). The approximated fixation mechanisms 14a, 14b are detached from the sheath 20 and excess shaft 12 (i.e., the portion of the shaft 12 that is not between the approximated fixation mechanisms 14a, 14b) and the sheath 20 is removed from the heart (FIG. 3D).

The direction of right ventricular papillary muscle approximation appropriate for a particular patient can depend on anatomical variations in the patient's heart. For instance, the direction of right ventricular papillary muscle approximation can be varied from the medial papillary muscle to the posterior papillary muscle. The direction of right ventricular papillary muscle approximation can also be changed vertically, e.g., toward the right ventricular apex 23, toward the tricuspid annulus 25, or perpendicular to the ventricular septum 28. The anatomy of each patient heart is variable and depends on a variety of factors including the etiology of the tricuspid regurgitation. As a result, the most appropriate direction of right ventricular papillary muscle approximation may also vary among patients.

For instance, when the tricuspid annulus is evenly dilated with a laterally dislocated anterior papillary muscle and a central tricuspid regurgitation, the anterior papillary muscle can be approximated toward the middle portion of the ventricular septum to treat the tricuspid regurgitation. When the tricuspid annulus is irregularly dilated (e.g., such that the anterior portion of the annulus is dilated more than the posterior portion), and with a dislocated papillary muscle and a central tricuspid regurgitation, the medial papillary muscle can be approximated toward the middle portion of the ventricular septum to treat the tricuspid regurgitation. In this case, if the anterior papillary muscle were to be approximated toward the middle portion of the ventricular septum, the anterior portion of the tricuspid annulus could potentially remain dilated, resulting in residual tricuspid regurgitation. In another example (not shown), when the posterior portion of the annulus is dilated more than the anterior portion, the posterior papillary muscle can be approximated toward the middle portion of the ventricular septum to treat the tricuspid regurgitation. When the tricuspid annulus is dilated and the heights of leaflet coaptation is the same between a septal leaflet and an anterior leaflet of the tricuspid valve and between the septal leaflet and a posterior leaflet of the tricuspid valve, the anterior papillary muscle can be approximated horizontally toward the ventricular septum. If the tricuspid regurgitation is due to prolapse of the anterior leaflet caused by elongated chordae tendiniae attached to the anterior leaflet, the papillary muscle can be approximated slightly toward the right ventricular apex, thus increasing the coaptation zone of each leaflet.

The extent of right ventricular papillary muscle approximation appropriate for a particular patient can depend on the anatomy and dimension of the patient's heart. For instance, in the approach to right ventricular papillary muscle approximation shown in FIGS. 3A-3H, the anterior papillary muscle 24 may not necessarily be fully approximated to the ventricular septum 28. The distance between the anterior papillary muscle 24 and the ventricular septum 28 is adjustable, e.g., from about 25% to 100% of the original distance between the anterior papillary muscle 24 and the ventricular septum 28.

The position of the device at the anterior papillary muscle 24 for a particular patient can also depend on the anatomy and dimension of the patient's heart. For instance, the size and shape of the anterior papillary muscle 24 of the right ventricle 21 can vary among patients. For a large anterior papillary muscle 24, the device may be positioned close to the head of the anterior papillary muscle because the head of the anterior papillary muscle has a large insertion of chordae tendinea and is close to the annulus and valve leaflet. For a small anterior papillary muscle 24 with a wide base, the device may be positioned at the base of the anterior papillary muscle 24. In some examples, the size and shape of the anterior papillary muscle can be evaluated, e.g., using an image-guiding modality, to inform the positioning of the device.

The outcome of the tricuspid regurgitation treatment can be evaluated and the direction and/or position of the device(s) can be adjusted if appropriate. For instance, the motion of the tricuspid valve and/or the extent of the reduction of the tricuspid regurgitation can be evaluated. The treatment can be evaluated by echocardiography or another image-guiding modality. For treatments performed under cardiopulmonary bypass, the treatment can be evaluated after the cardiopulmonary bypass has been removed and the heart has been restarted.

Right Ventricular Papillary Muscle Approximation with Multiple Devices

In some examples, multiple devices 10 can be combined into an assembly that enables the position of the anterior papillary muscle 24 to be adjusted more precisely. For instance, one or more devices can be fixed on the ventricular septum 28 and connected to one or more devices fixed on the anterior papillary muscle 24. The distance between devices can be adjusted, e.g., by a string or wire connecting the devices, after placement of all of the devices. For instance, the length and/or tension of the strings can be adjusted to control the relative distance and position of the devices.

Figure 4A:
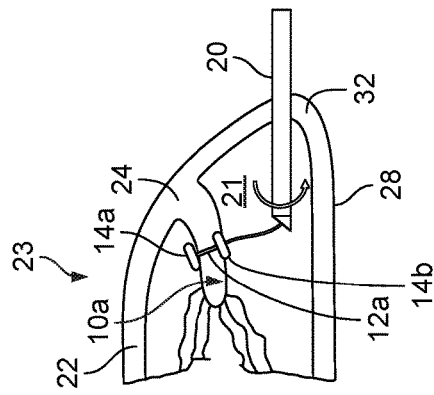
FIGS. 4A-4D are diagrams of an approach for deploying two devices in the heart.
Figure 4B:
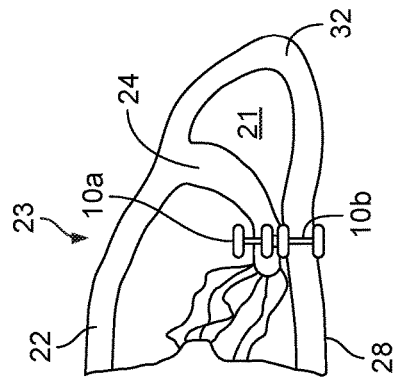

FIGS. 4A-4D show one approach to right ventricular papillary muscle approximation using an assembly including two devices 10a, 10b. The devices can be inserted into the right ventricle 21 of the heart 23 from a right ventricular apex 32. To deploy the first device 10a, the sheath 20 containing the first device is introduced into the right ventricle 21 through the right ventricular apex 23. A shaft of the first device is advanced from the sheath 20 to penetrate the anterior papillary muscle 24. The shaft may penetrate the anterior papillary muscle 24 at a middle portion of the papillary muscle (as shown in the illustrated embodiment), at a head portion of the papillary muscle, or at a base portion of the papillary muscle. A first fixation mechanism 14a is deployed at a distal end of the first shaft between the anterior papillary muscle 24 and the right ventricle free wall 22 (FIG. 4A). A second fixation mechanism 14b is deployed toward a proximal end of the shaft. An approximation mechanism (e.g., the approximating mechanism 15 shown in FIGS. 1A and 1B) such as a string, wire, or thread is pulled to approximate the first and second fixation mechanisms 14a, 14b, locking the first device 10a onto the anterior papillary muscle 24 (FIG. 4B).

Figure 4C:
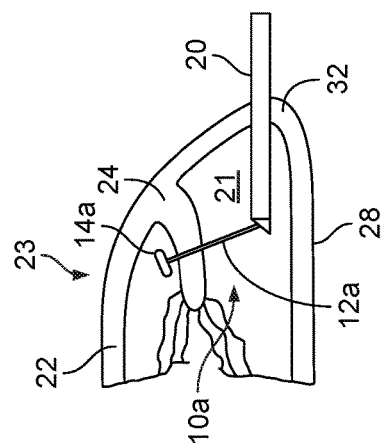

To deploy the second device 10b, the sheath 20 is rotated and a shaft of the second device is advanced through the ventricular septum 28. A first fixation mechanism 14c of the second device is deployed at a distal end of the shaft. A second fixation mechanism 14d of the second device is deployed toward a proximal end of the shaft. An approximation mechanism, such as a string, wire, or thread (not shown), is pulled to approximate the first and second fixation mechanisms 14c, 14d, locking the second device 10b onto the ventricular septum 28 (FIG. 4C).

Figure 4D:
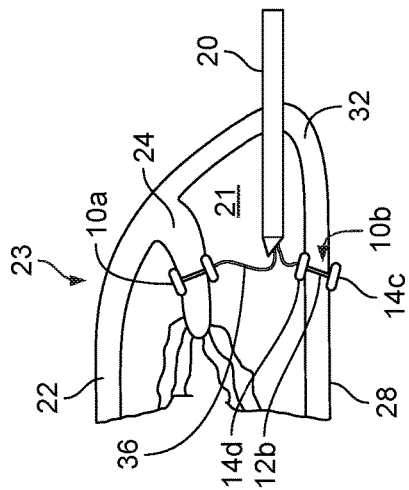

The proximal ends of the first and second devices 10a, 10b are connected to the distal end of the sheath 20 by a connector 36, such as a string, wire, or thread. The connector 36 is pulled in order to shorten the distance between the anterior papillary muscle 24 and the ventricular septum 28. The connected first and second devices are detached from the sheath and excess shaft 12a, 12b and the sheath 20 is removed from the heart (FIG. 4D). The connector 36 may be formed of metal (e.g., nitinol), suture, or other material.

Figure 5A:
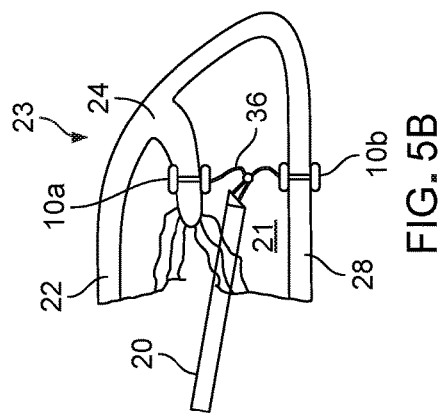
FIGS. 5A-5C are diagrams of another approach for deploying two devices in the heart.
Figure 5B:
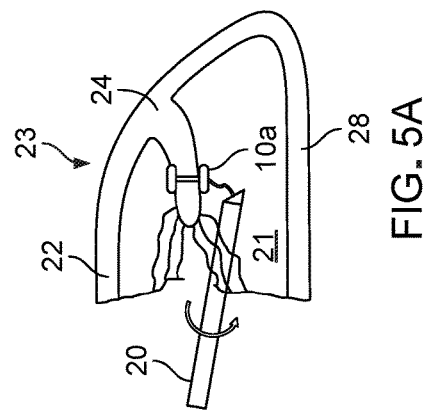
Figure 5C:
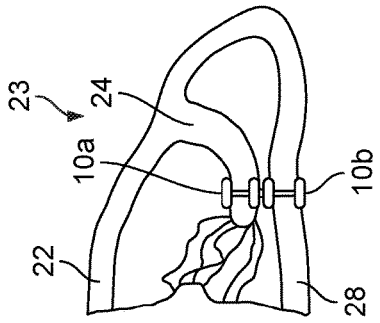

Referring to FIGS. 5A-5C, in another approach, multiple devices 10a, 10b can be inserted into the right ventricle 21 of the heart 23 from a right atrium 38. To deploy the first device 10a, the sheath 20 is introduced through the right atrium 38 and a tricuspid valve 40. A shaft of the first device is advanced from the sheath 20 to penetrate the anterior papillary muscle 24. The shaft may penetrate the anterior papillary muscle 24 at a middle portion of the papillary muscle (as shown in the illustrated embodiment), at a head portion of the papillary muscle, or at a base portion of the papillary muscle. A first fixation mechanism 14a of the first device is deployed at the distal end of the shaft between the anterior papillary muscle 24 and the right ventricle free wall 22. A second fixation mechanism 14b is deployed toward the proximal end of the shaft. An approximation mechanism (e.g., the approximating mechanism 15 shown in FIGS. 1A and 1B) is pulled to approximate the first and second fixation mechanisms 14a, 14b, locking the first device 10a onto the middle portion of the anterior papillary muscle 24 (FIG. 5A).

To deploy the second device 10b, the sheath 20 is rotated and of the second device is advanced through the ventricular septum 28 (FIG. 5D). A first fixation device 14c of the second device is deployed at a distal end of the shaft. A second fixation device 14d of the second device is deployed toward the proximal end of the shaft. An approximation mechanism (e.g., the approximating mechanism 15 shown in FIGS. 1A and 1B) is pulled to approximate the first and second fixation mechanisms 14c, 14d, locking the second device 10b onto the ventricular septum 28 (FIG. 5B).

The proximal ends of the first and second devices are connected to the distal end of the sheath 20 by the connector 36 that serves as an approximation mechanism. The connector is pulled toward the sheath 20 in order to shorten the distance between the anterior papillary muscle 24 and the ventricular septum 28. The connected first and second devices are detached from the sheath and excess shaft and the sheath 20 are removed from the heart (FIG. 5C).

Using multiple devices enables both the horizontal and the vertical position of the devices to be adjusted within the three-dimensional geometry of the right ventricle 21. The devices can be positioned under the guidance of an imaging modality, such as echocardiography, and can be performed in a beating heart or an arrested heart. In some examples, sensors can detect the position of the anterior papillary muscle 24 and/or information about the length and tension of each connector 36. Based on data from the sensors and/or under the guidance of an imaging modality, the length and tension of the strings can be adjusted to achieve a desired position for the RV-PMA assembly. By adjusting the length and tension of the strings according to guidance from sensors and/or from an imaging modality, the possibility of breaking the strings due to high tension, and thus damaging the cardiac tissue, can be mitigated.

In some examples, more than two devices can be deployed. For instance, two or more devices can be applied to the ventricular septum, e.g., to enable further precision in adjustments of the Fixation and Locking Mechanisms for Right Ventricular Papillary Muscle Approximation Devices Various fixation mechanisms can be used to anchor the proximal and distal ends 16, 18 of the device 10 to cardiac tissue.

Figure 6:
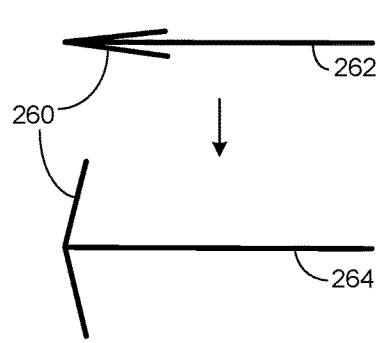
FIG. 6 is a diagram of a hook fixation mechanism.

Referring to FIG. 6, in one example, an arrow-shaped hook 260 can be used as the fixation mechanism. When the device is contained within the sheath, the hook 260 is folded against the shaft in a closed position 262. When the device is deployed, the hook 260 unfolds into an open position 264. In some examples, a locking mechanism 264, such as a ratchet mechanism, can lock the hook in the open position 264 after deployment. The locking mechanism 264 can also be unlocked such that the hook 260 recovers its closed position 262, for instance, to enable repositioning of the device.

Figure 7A:
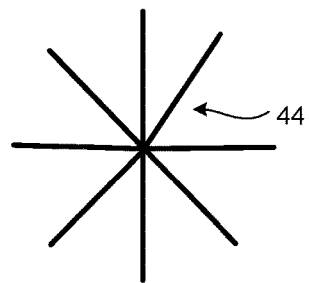
FIG. 7A is a diagram of an anchor fixation mechanism.

Referring to FIG. 7A, in one example, one or more anchors 44 can be used as the fixation mechanism. The number of anchors 44 at each end of the device can be adjusted according to the force expected to be applied to the device. The anchors can be folded into the sheath during insertion, unfolded upon deployment, and folded again if appropriate for repositioning of the device. For instance, the anchors can be folded by pulling the anchors beyond a threshold tension. A locking system (not shown) can be used to lock the anchors in an open (unfolded) position once the position of the device is confirmed.

Figure 7B:
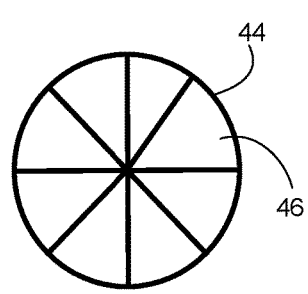
FIG. 7B is a diagram of a disc fixation mechanism including an anchor.

Referring to FIG. 7B, in one example, a soft disc 46 including anchors 44 can be used as the fixation mechanism. The disc can be made of a soft material, such as an elastic polymer. The anchors 44 can provide skeletal reinforcement to the disc. In its closed position, e.g., when contained within the sheath, the disc 46 can be folded into the sheath like an umbrella.

Figure 8A:
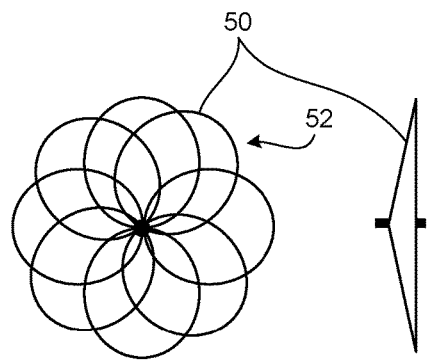
FIGS. 8A and 8B are diagrams of an umbrella fixation mechanism.
Figure 8B:
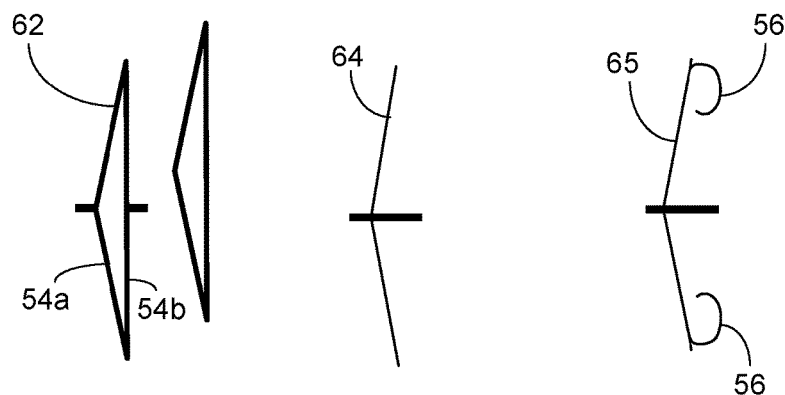

Referring to FIG. 8A, in one example, an umbrella 50 can be used as the fixation mechanism. The umbrella 50 can be formed of multiple thin metal wires 52, e.g., nitinol wires. Each wire 52 is formed into a round or oval shape (as seen in a top view 53) such that the multiple wires 52 together form an umbrella structure (as seen in a side view 55). In some examples, a thin membrane made of, e.g., Dacron®, elastic polymer, or another material, can be inserted into the umbrella structure formed by the wires 52 to prevent shunt blood flow from the left ventricle to the right ventricle through the umbrella structure. Referring to FIG. 8B, other umbrella structures are also possible. For instance, an umbrella 62 can include two membranes 54a, 54b. An umbrella 64 can be formed of wires that maintain their round or oval shape when folded but cause the angle of umbrella to change upon opening. An umbrella 65 can be formed of a single membrane with a hook portion 56 that can grab tissue when the umbrella 65 is unfolded.

Referring to FIGS. 9A and 9B, an umbrella device 220 includes distal and proximal two-membrane umbrellas 62a, 62b as the fixation mechanism. In its folded state (FIG. 9A), the umbrellas 62a, 62b are collapsed and the umbrella device 220 can be contained in a sheath, e.g., for insertion into the heart. The umbrellas 62a, 62b are self-expandable and expand upon deployment of the umbrella device 220 (FIG. 9B).

Referring to FIGS. 10A and 10B, in one example, a balloon device 70 includes distal and proximal balloons 48a, 48b as the fixation mechanism. The balloons 48a, 48b can be deflated for introduction into the heart and inflated when the balloon device 70 is deployed. In one example, the balloons 48a, 48b are 3 mL balloons. In its folded state (FIG. 10A), the balloons 48a, 48b are deflated and a balloon device 70 can be contained in the sheath 20. To deploy the balloon device 70, a fluid such as saline can be introduced into each balloon 48a, 48b through a small tube (not shown) to inflate the balloons 48a, 48b (FIG. 10B).

Figure 11A:
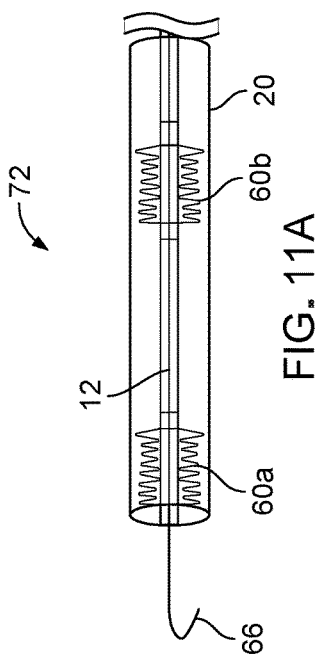
FIGS. 11A and 11B are diagrams of a device including another balloon fixation mechanism in a folded state and a deployed state, respectively.
Figure 11B:
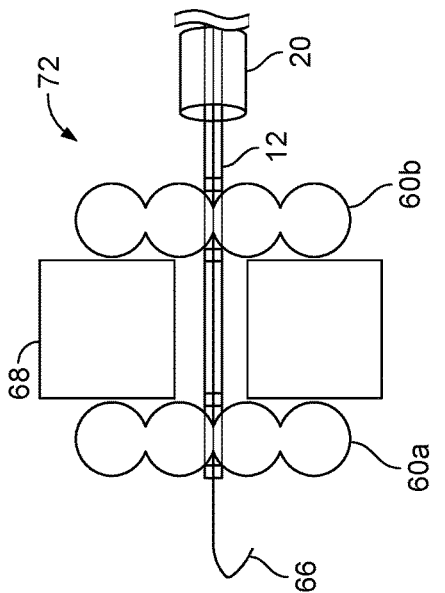

In some examples, the diameter of the balloons can be large compared to the ventricular geometry. For instance, referring to FIGS. 11A and 11B, the fixation mechanism on a balloon device 72 includes two different sizes of balloon discs 60a, 60b aligned concentrically at the distal and proximal ends, respectively, of the device 72. The balloon discs 60a, 60b are connected by gateways 75. The balloon discs 60a, 60b provide a larger surface area against the surface of the cardiac tissue with minimal loss of ventricular volume as compared to large balloons (e.g., balloons 48a, 48b shown in FIGS. 10A and 10B), thus keeping the balloon device 72 fixed in position and resistant to displacement resulting from heart activity.

Figure 12A:
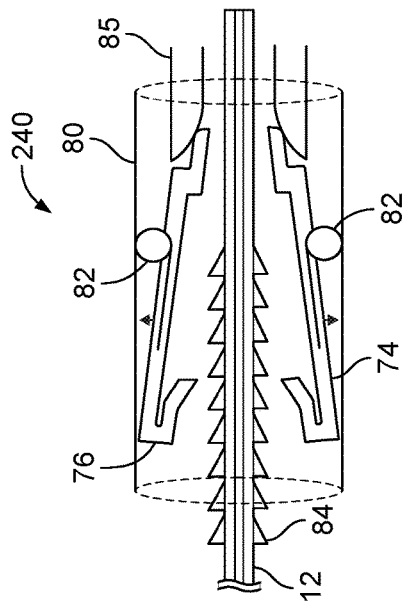
FIGS. 12A and 12B are diagrams of an example ratchet mechanism.
Figure 12B:
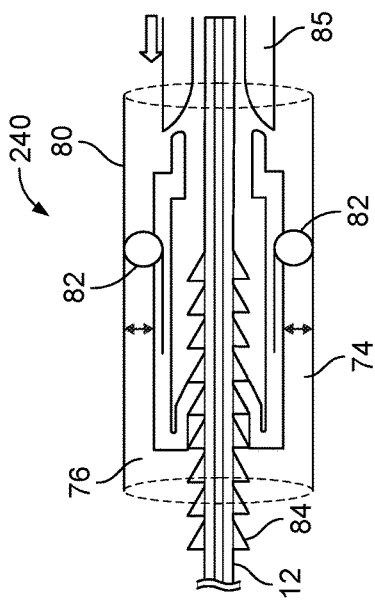

Referring to FIGS. 12A and 12B, papillary muscle approximation can be performed by adjusting the length of the device, i.e., by drawing the fixation devices together. A locking mechanism, e.g., attached to a proximal end of the device, can be used to fix the length of the device. In one example, a ratchet mechanism 240 can be used to adjust the length of the shaft 12. In the ratchet mechanism 240, a tube 74 with hooks 76 can be pushed along a threaded internal shaft 78. The tube 74 is at least partially contained within an outer tube 80 and biased against the outer tube 80 by one or more springs 82. A control device 85 at a proximal end of the tube 74 is used to position the tube 74 at the desired position along the threaded internal shaft 78. In particular, when the control device 85 exerts a force on the tube 74, the ratchet mechanism 240 is unlocked, causing the tube 74 to move toward a distal end 78 of the shaft 78. When the force exerted by the control device 85 is removed, the springs 82 cause the tube 74 to close around the shaft 78, locking the tube 74 in position. In some examples, only the tube 74 and internal shaft 78 are provided. In this configuration, the tube 74 can be positioned along the internal shaft 78 by applying a force to the tube 74, but it can be difficult to reposition the tube 74 along the shaft 78.

Figure 13:
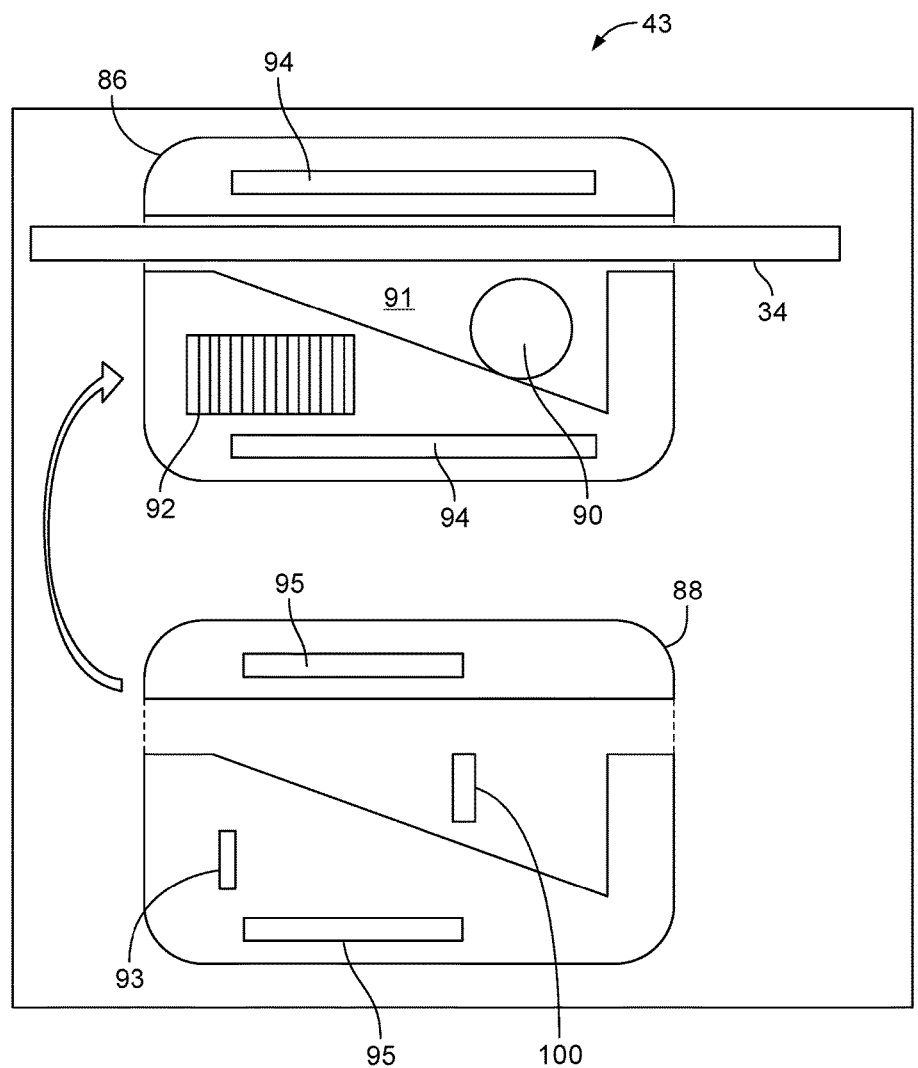
FIG. 13 is a diagram of an example locking mechanism.

FIG. 13 shows another example of a locking mechanism 43 for adjusting and locking the length of the shaft of the device. The locking mechanism 43 is a modified ratchet system that includes a main portion 86 (FIG. 13), an accessory portion 88, and a ball 90 disposed within a cavity 91 in the device. The locking mechanism 43 includes a thread 92 and catch 93 for a ratchet system for fixing the position of the locking mechanism. Rails 94, 95 enable the accessory portion 88 to slide relative to the main portion 86 (or vice versa) to lock the locking mechanism 43. When assembled, the accessory portion 88 is disposed onto the main portion 86. The string 34 or the connector 36 can be threaded through the assembled locking mechanism 43. After the device is positioned in the heart (e.g., after the fixation mechanisms are deployed), the string 34 can be pulled, adjusting the length of the device 10. If multiple devices are used, the string 34 can be pulled to adjust the distance between devices 10.

Figure 14A:
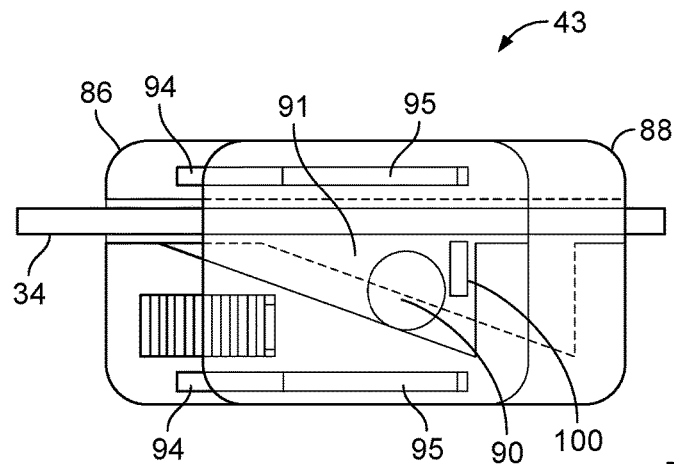
FIGS. 14A-14C are diagrams showing the operation of the locking mechanism of FIG. 13.
Figure 14B:
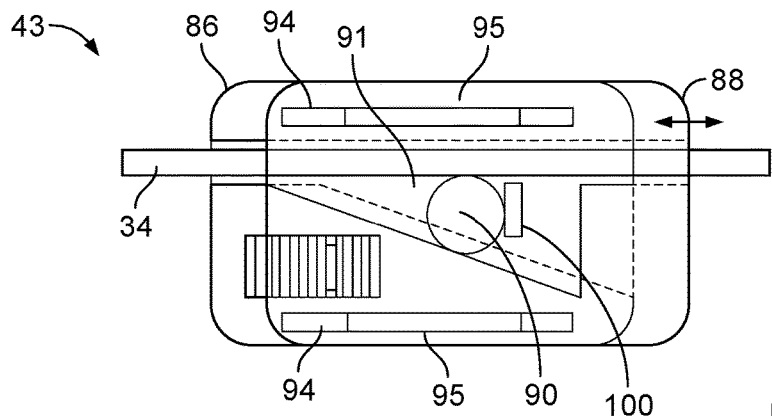
Figure 14C:
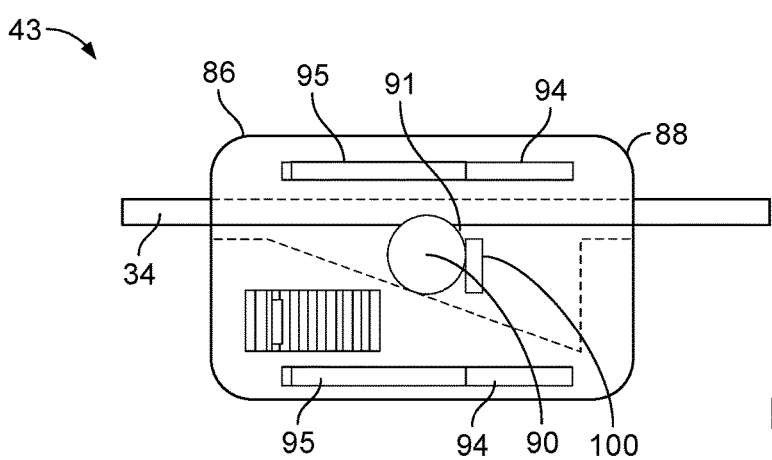

FIGS. 14A-14C show the operating mechanism for the locking mechanism 4.3 In an unlocked state (FIG. 14A), the ball 90 is free to move within the cavity 91, and the accessory portion 88 can slide over the main portion 86 in order to push the ball 90. In a half locked state (FIG. 14B), the accessory portion 88 is slid relative to the main portion 86 such that the overlap between the accessory portion 88 and the main portion 86 is increased. In the half locked state, a ball pusher 100 causes the ball 90 to contact the string 34 but not to compress the string. In a locked state (FIG. 14C), the accessory portion 88 is slid further relative to the main portion 86 such that there is substantially complete overlap between the accessory portion 88 and the main portion 86. In the locked state, the ball 90 compresses the string 34, fixing the position and hence the length of the string 34. A ratchet mechanism, such as the ratchet mechanism 240 of FIGS. 12A-12B, can also be combined with the locking mechanism 43.

Figure 15:
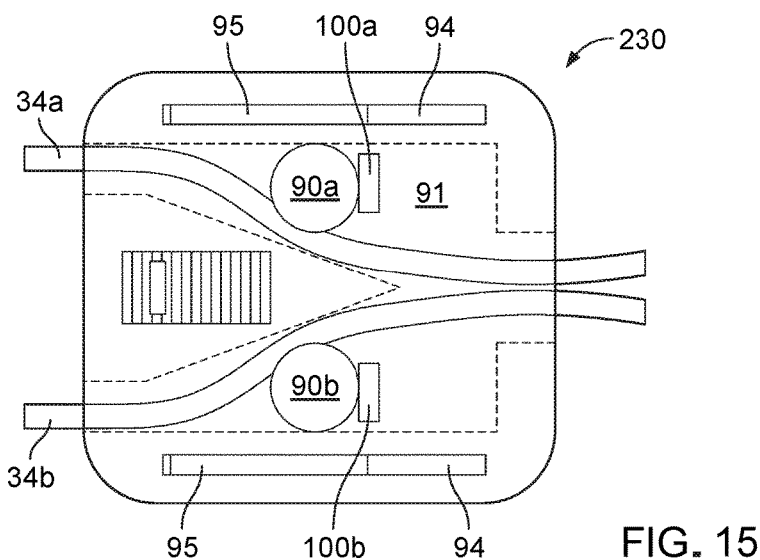
FIG. 15 is a diagram of an example locking mechanism for multiple devices.

FIG. 15 shows an example locking mechanism 230 that can lock two strings 34a, 34b or two connectors 36 simultaneously. The locking mechanism 230 can be used, e.g., as a connector for connecting strings from multiple devices 10 (e.g., as the connector 36 shown in FIGS. 4A-4I). Two sets of balls 90a, 90b and ball pushers 100 provide the capability to lock both strings 34a, 34b.

Figure 16A:
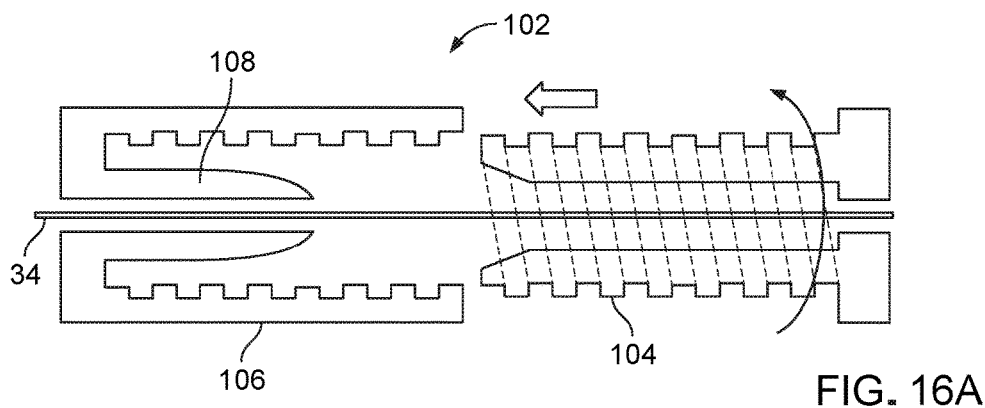
FIGS. 16A and 16B are diagrams of an example screw locking mechanism.
Figure 16B:
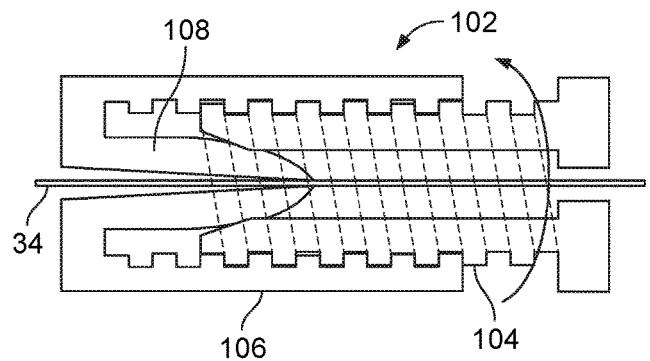

Referring to FIGS. 16A and 16B, the shaft length can also be adjusted using a screw mechanism 102. A male-threaded screw 104 is inserted into a female-threaded screw 106, causing a central portion 108 of the female-threaded screw 106 to be squeezed by a tip 110 of the male-threaded screw 104 (FIG. 22B). The string 34 or connector 36 can be inserted through the central portion 108 of the female-threaded screw 106 and can be fixed in position when the central portion 108 is squeezed by the male-threaded screw 104.

Figure 17A:
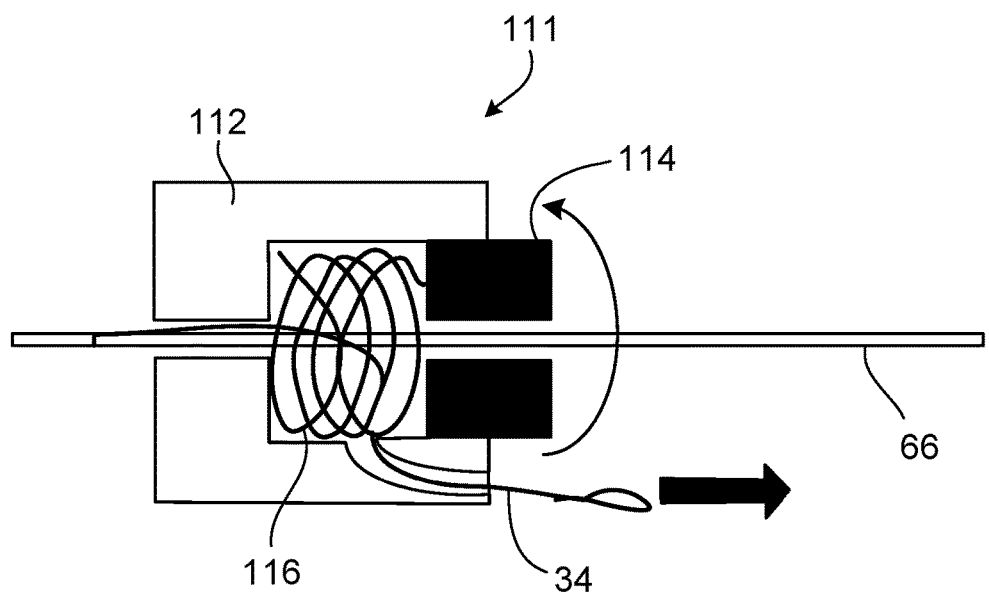
FIGS. 17A and 17B are diagrams of example screw locking mechanisms.
Figure 17B:
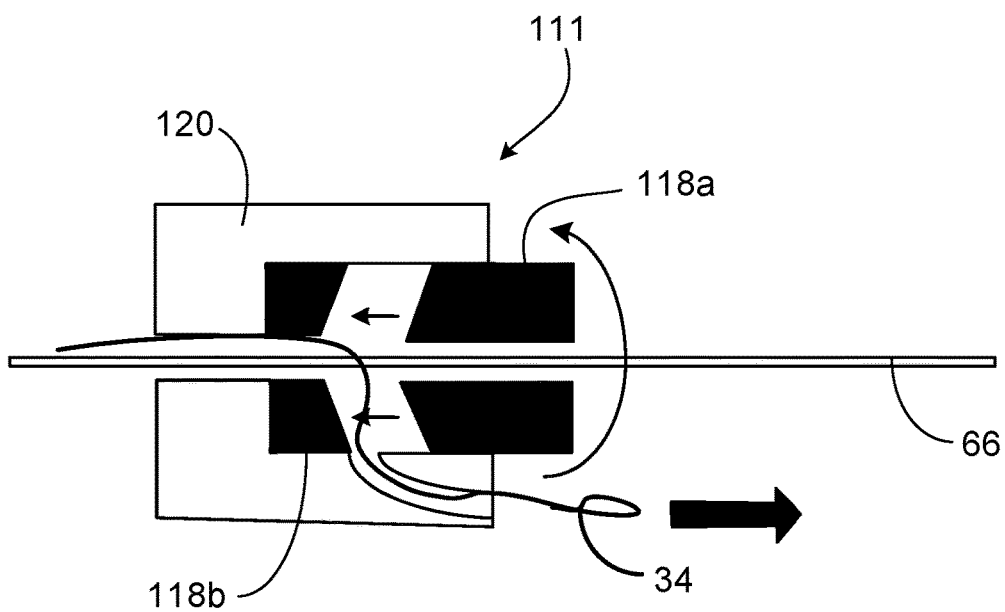

FIG. 17A shows a locking mechanism 111 for locking the position of a string 34. A male-threaded set screw 114 is screwed into a female-threaded set screw 112, causing a compression spring 116 to be compressed. The compressed spring 116 fixes the position of the string 34 or connector 36. FIG. 17B shows a locking mechanism 113 for locking the position of the string 34 or connector 36. A male-threaded convex set screw 118a and a male-threaded concave set screw 118b are combined with a female-threaded set screw 120 and the string 34 is threaded through a gap between the male convex set screw 118a and the male concave set screw 118b. By rotating the male convex set screw 118a, the male convex set screw 118a and the male concave set screw 118b are moved closer and can fix the string in position. To reposition the device, the screws in the various screw-based locking mechanisms described herein can be unscrewed (i.e., rotated in the opposite direction), releasing the string 34 or connector 36.

Deployment System for Right Ventricular Papillary Muscle Approximation Devices

The devices for right ventricular papillary muscle approximation described herein can be deployed in an arrested heart (i.e., in open heart surgery) or in a beating heart. Image-guiding modalities, such as echocardiography, fluoroscopy, or magnetic resonance can be used to guide the positioning of the devices in the heart. Catheter-based techniques can be used to introduce the device into the heart.

The right ventricular papillary muscle approximation can be achieved surgically by midline sternotomy or thoracotomy, endoscopically or thoracoscopically with minimal incision, or by another approach. These approaches can be performed as open-heart procedures with cardiac arrest or can be performed in a beating heart without cardiopulmonary bypass. In an open-heart approach, some or all of the devices 10 can be replaced and/or augmented with sutures since the anatomical structures of the tricuspid annulus, the papillary muscles of the right ventricle, and the septum are all visible. In some examples, a transcatheter approach from the left ventricular side can also be used, for instance when a tricuspid valve and papillary muscle are treated at the same time as a mitral or aortic valve is treated or at the same time as a left ventricular papillary muscle is treated transcatheterly. In addition, for approaches from the epicardial side of the heart (e.g., the approach of FIGS. 2A-2H), right ventricular papillary muscle approximation can be achieved with catheter-based interventions using small sternotomy or thoracotomy or endoscopy.

In some examples, approaches can be made from the right atrium (see, e.g., FIGS. 5A-5F). The right atrium gathers blood flow from the whole body via the superior vena cava and the inferior vena cava. For approaches from the right atrium, right ventricular papillary muscle approximation can be achieved with a catheter-based intervention through a peripheral vein, such as the jugular vein or the femoral vein.

Figure 18A:
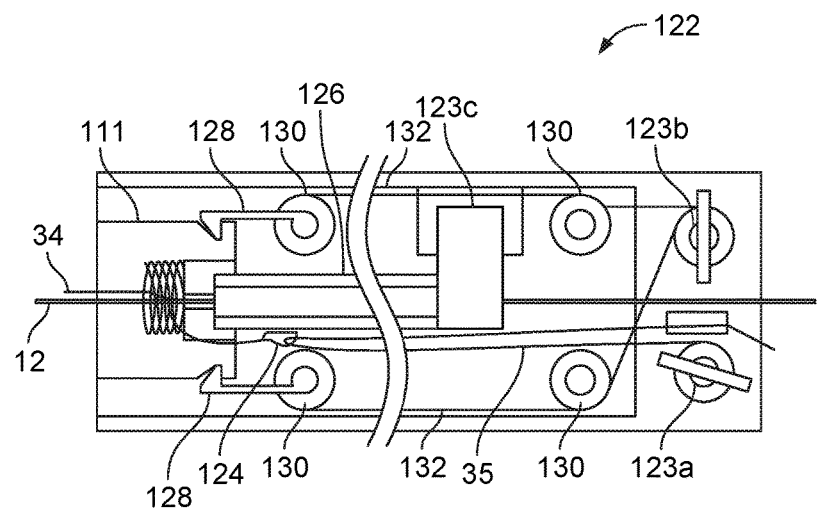
FIGS. 18A and 18B are diagrams of an example deployment system.
Figure 18B:
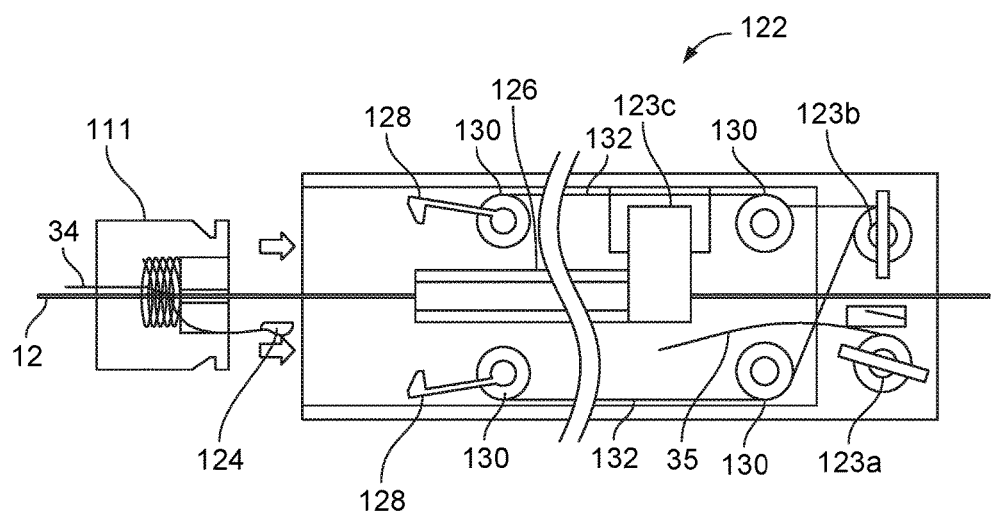

Referring to FIGS. 18A and 18B, an example deployment system 122 with a screw-based locking mechanism, such as the locking mechanism 111, can be used to approximate the fixation mechanisms of devices. The length of the device is determined by pulling the string 34 using the deployment system 122. A loop 124 is formed at the proximal end of the string 34 and a second string 35 is interposed through the loop 124. The second string 35 is connected to a lever 123a at a proximal end of the deployment device 122. The locking mechanism 111 is connected to the deployment system 122 by one or more hooks 128, which are connected to wheels 130 and to a lever 123b via wires 132. A hexagonal wrench 126 is connected to a hexagonal socket (not shown) at the center of a male set screw 114 and can be rotated by a lever 123c.

To operate the deployment system 122, the lever 123a is wound to pull the second string 35 proximally into the deployment system 122, causing the device string 34 to be pulled via its loop 124 connection to the second string 35. While the strings 34, 35 are being pulled, the hexagonal wrench is rotated by the lever 123c in order to rotate the male set screw 114, fixing the string 34 length and position (FIG. 18A). The second string 35 is then cut, e.g., by accessing the string through a window 37, in order to release the device string 34. The lever 123b is rotated to wind the wires 132, which pull the hooks 128 connected to the proximal end of the device 10. As a result, the hooks 128 are disengaged from the locking mechanism 111 and the device 10 can be released from the deployment system 122 (FIG. 18B).

Right Ventricular Papillary Muscle Approximation Devices with Contracting Bands

In some examples, a contracting band can be incorporated into right ventricular papillary muscle approximation devices, such as the devices described above, to help improve cardiac output. A uniaxial actuator, such as a passive actuator (e.g., a spring) or an active actuator (e.g., an electromagnetic actuator or a soft robotics actuator) can be included in the shaft of a device and/or in a band connecting two devices. A bioengineered actuator, such as an artificial muscle actuator grown by cell seeding, can also be used. The actuator can be positioned between the ventricular septum and the papillary muscle or right ventricular free wall to assist with the right ventricular pumping function by exerting a force that brings the ventricular septum and the papillary muscle or right ventricular free wall together, resulting in increased ejection fraction and improved cardiac output. For instance, the actuator can be incorporated into the shaft 12 of a single device 10 and/or can be incorporated into one or more connectors 36 connecting multiple devices 10.

Figure 19:
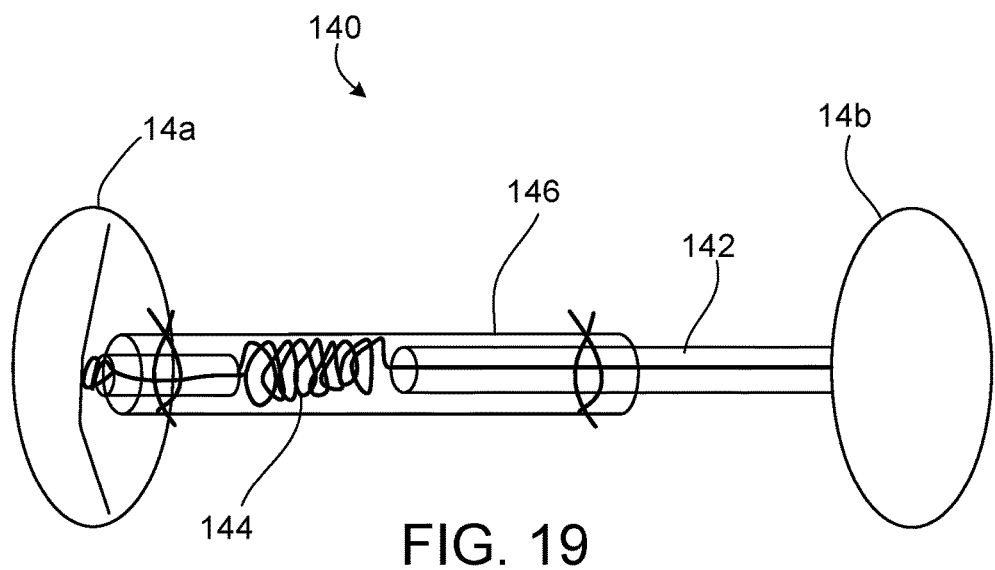
FIG. 19 is a diagram of a spring actuated band.

For instance, referring to FIG. 19, a passive actuating band 140 can include a shaft 142 with a passive actuator, such as a spring 144 (e.g., a stainless steel spring). The shaft 142, including the elastic portion 144, can be contained within a protective cover 146, such as a polytetrafluoroethylene cover. When the device is deployed in the heart, the elastic portion 144 expands during diastole. The spring exerts a recoil force on the shaft 142, which can assist right ventricular pumping function and hence improve cardiac output. The actuating band 140 can be incorporated into, e.g., the shaft 12 of a single device 10 or a connector 36 connecting multiple devices.

Figure 20A:
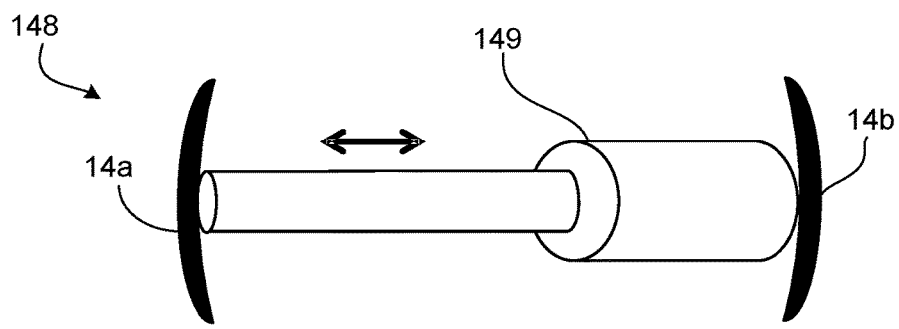
FIGS. 20A and 20B are diagrams of bands actuated by an electromagnetic actuator and a soft robotics actuator, respectively.
Figure 20B:
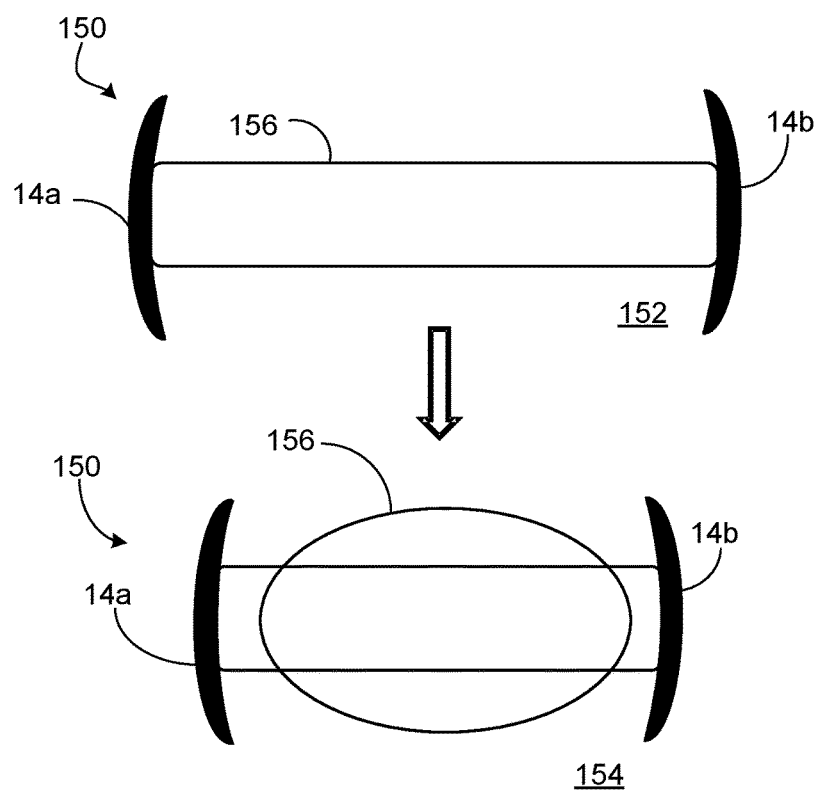

Referring to FIGS. 20A and 20B, active actuators such as an electromagnetic actuator 148, such as a solenoid-rod couple 149, or a soft robotics actuator 150 can apply dynamic force in accordance with a patient's specific cardiac electrophysiological and kinematic characteristics of the right ventricle. The actuation can be synchronized with the patient's electrocardiogram. An active actuator can be powered by a power source, such as an implantable power source. In some cases, the actuators may further assist with the right ventricular pumping function by volume changes. For instance, the soft robotics actuator 150 can include a fluid inflatable actuator 156 that changes from a deflated state 152 to a swollen state 154 upon recoil, displacing blood from the right ventricle.

EXAMPLES

The invention is further described in the following examples, which do not limit the scope of the invention described in the claims.

The following examples generally show an evaluation of right ventricular papillary approximation as a treatment for tricuspid regurgitation in comparison with standard tricuspid annuloplasty techniques. The examples further demonstrate the mechanical properties of the tethering mechanism of a device for right ventricular papillary approximation.

Example 1

Ex Vivo Use of Right Ventricular Papillary Approximation as Treatment for Tricuspid Regurgitation To evaluate the techniques described herein, right ventricular papillary approximation was performed on an experimentally produced tricuspid regurgitation and compared to a tricuspid annuloplasty.

Right ventricles of isolated porcine hearts (n=10) were statically pressurized (44 mmHg) in a saline-filled tank, leading to right ventricle dilation and central tricuspid regurgitation. Tricuspid regurgitant flow in a right ventricle was measured with a saline-filled column connected to the saline-filled tank 104 in which the right ventricle was immersed.

Figure 21A:
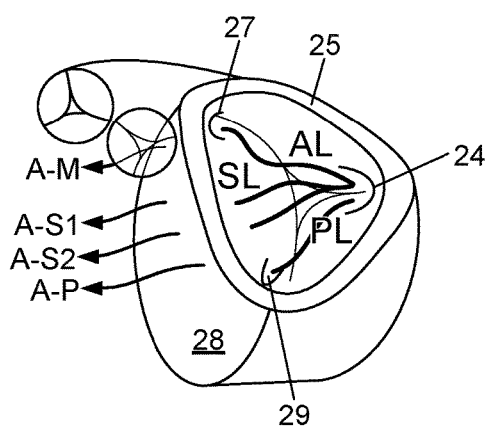
FIGS. 21A-21D are cross-sectional diagrams of a right ventricle.
Figure 21B:
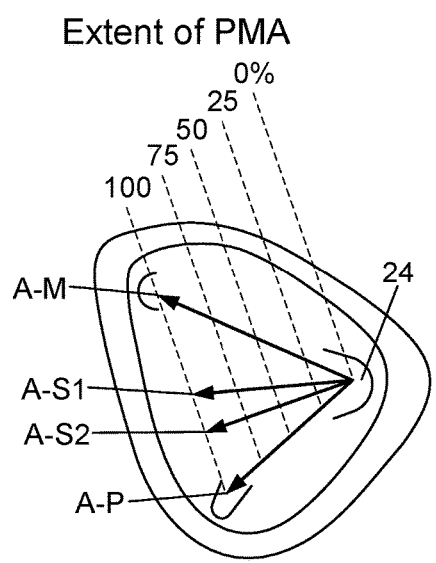

Referring to FIG. 21A, for a right ventricular papillary approximation treatment, the head of the anterior papillary muscle 24 was approximated to four sites on the ventricular septum 28 between the medial 27 and posterior 29 papillary muscles: the medial papillary muscle (site A-M), the posterior papillary muscle (site A-P), the midpoint between the medial papillary muscle and the posterior papillary muscle (site A-S1), and the intersection of the septum 28 and its perpendicular line on the anterior papillary muscle 24 (site A-S2). Referring to FIG. 21B, the extent of papillary muscle approximation was adjusted from 0% (the initial position prior to approximation) to 100% (full contact between the anterior papillary muscle 24 and the septum 28). For tricuspid annuloplasty, a prosthetic ring was implanted. A combined treatment was also formed in which a prosthetic ring was implanted followed by a right ventricular papillary approximation.

Figure 21C:
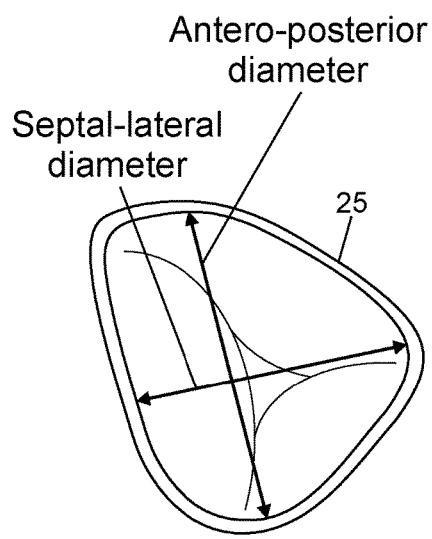
Figure 21D:
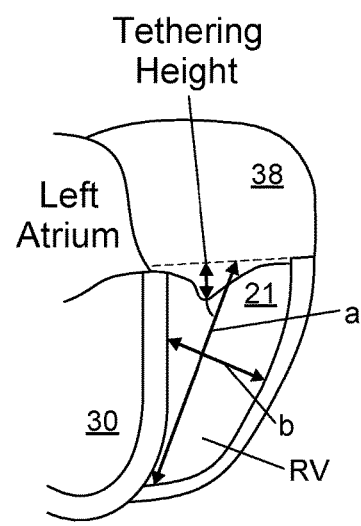

For each treatment, the annular dimension of the tricuspid valve 40 (FIG. 21C), the right ventricular volume, the right ventricular sphericity index (RVSI=b/a), and the tricuspid valve tethering (FIG. 21D) were analyzed by three-dimensional echocardiography.

Figure 22A:
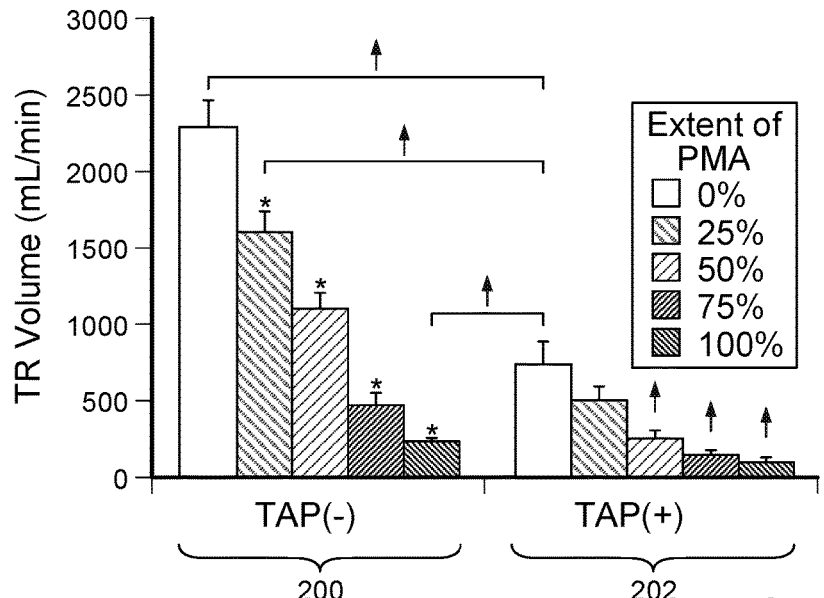
FIGS. 22A and 22B are graphs of the flow volume of tricuspid regurgitation for various extents and various directions, respectively, of right ventricular papillary approximation, with or without tricuspid annuloplasty.
Figure 22B:
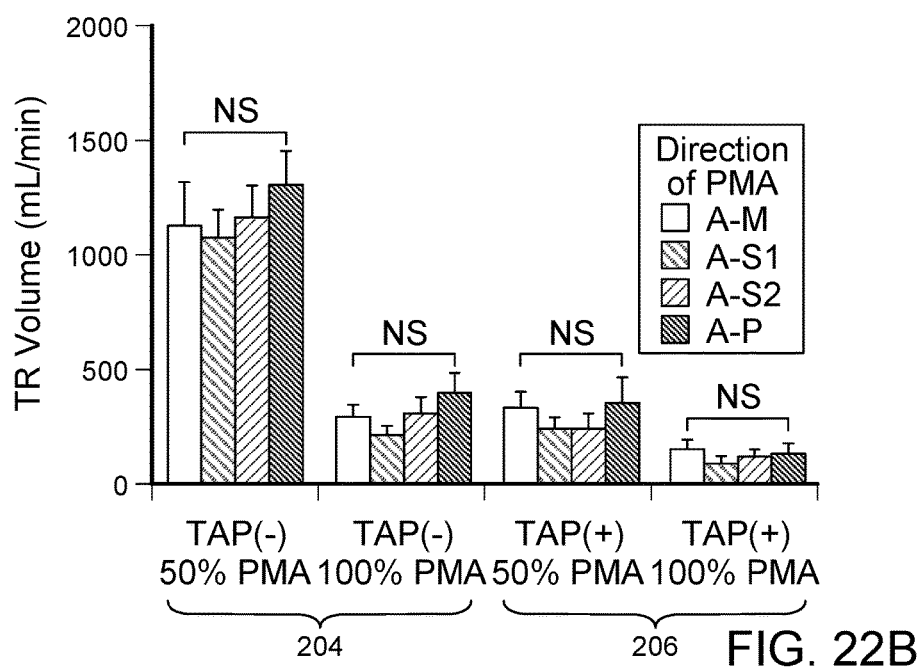

FIG. 22A shows a graph of the flow volume of tricuspid regurgitation for treatments with various extents of right ventricular papillary approximation (PVA) without (set 200) and with (set 202) tricuspid annuloplasty (TAP). FIG. 22B shows a graph of the flow volume of tricuspid regurgitation for treatments with various directions of right ventricular papillary approximation without (set 204) and with (set 206) tricuspid annuloplasty As shown in FIGS. 22A and 22B, the initial tricuspid regurgitation prior to treatment (i.e., 0% PVA) was measured at 2270±189 mL/min. Right ventricular papillary approximation alone reduced the tricuspid regurgitation to 214±45 mL/min (p<0.5) for 100% PVA. Combined right ventricular papillary approximation and tricuspid annuloplasty further reduced the tricuspid regurgitation to 80±39 mL/min. The direction of the papillary approximation did not significantly change the flow volume of the tricuspid regurgitation.

Figure 23E:
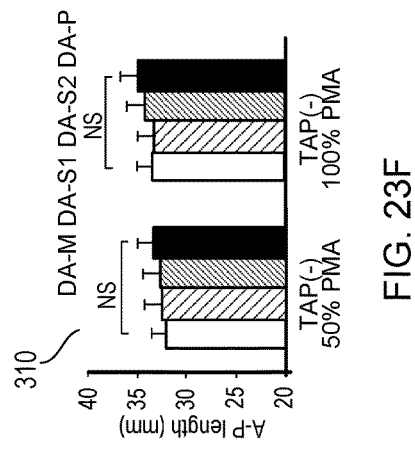
FIGS. 23E and 23F are graphs of the anterior-posterior dimension of the tricuspid annulus with tricuspid annuloplasty and various extents of right ventricular papillary approximation.
Figure 23F:
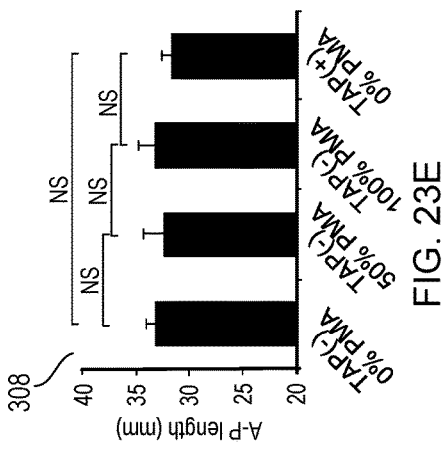

The shape of the tricuspid annulus was affected by the direction of the papillary approximation. As shown in graphs 300, 302 of FIGS. 23A-23B, the tricuspid annular area was reduced by 23% (p<0.05) by reducing the septal-lateral dimension of the annulus by 25% (p<0.5). As shown in graphs 304, 306 of FIGS. 23C-23D, among the directions of papillary approximation, A-M (anterior papillary muscle to medial papillary muscle) changed the annular shape most remarkably and reduced the septal-lateral annular dimension by the greatest extent. As shown in graphs 308, 310 of FIGS. 23E-23F, the anterior-posterior dimension of the tricuspid annulus did not change significantly regardless of the direction of papillary approximation.

Figure 24A:
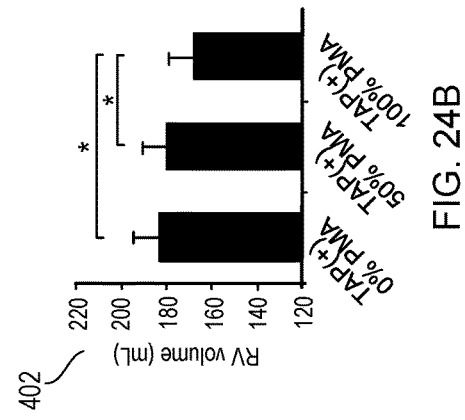
FIG. 24A is a graph of the right ventricular sphericity index (RVSI) for various extents of right ventricular papillary approximation.
Figure 24B:
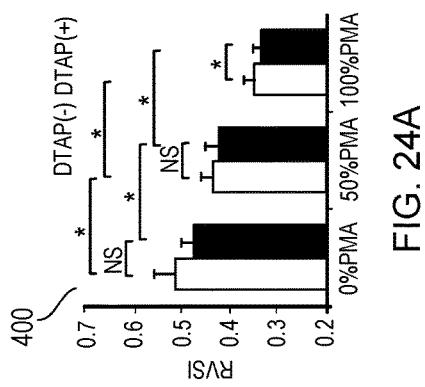
FIGS. 24B and 24C are graphs of right ventricular volume and tethering height, respectively, for various extents of right ventricular papillary approximation.
Figure 24C:
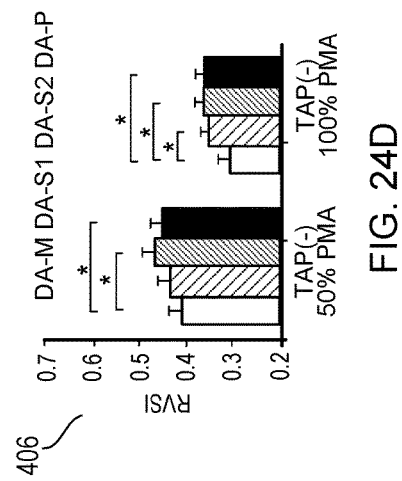
Figure 24D:
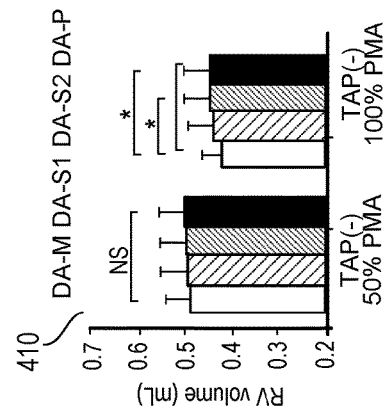
FIGS. 24D and 24E are graphs of RVSI and right ventricular volume, respectively, for various extents and directions of right ventricular papillary approximation.
Figure 24E:
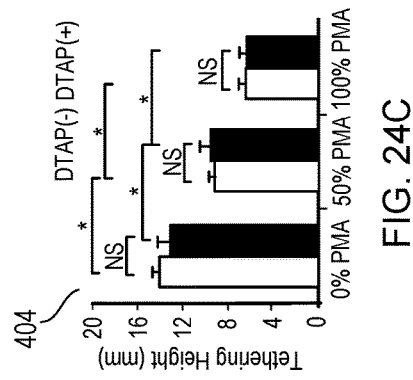
Figure 24F:
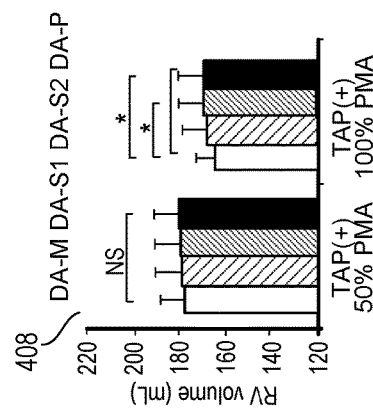

Referring to graphs 400, 402 of FIGS. 24A-24B, right ventricular papillary approximation restored the right ventricular geometry from spherical to a substantially normal shape and reduced the RVSI (p<0.05) and right ventricular volume. Right ventricular papillary approximation also reduced the tricuspid valve tethering height (p<0.05), as shown in a graph 404 of FIG. 24C. In contrast, tricuspid annuloplasty did not significantly reduce RVSI or tricuspid valve tethering. Among the directions of papillary approximation, A-M reduced RVSI and right ventricular volume the most, as shown in graphs 406, 408 of FIGS. 24D-24E, but no differences were observed in valve tethering, as shown in graph 410 of FIG. 24F.

This ex vivo study shows that right ventricular papillary approximation can repair tricuspid regurgitation better than tricuspid annuloplasty by simultaneously improving ventricular sphericity, valve tethering, and annular dimension. Although the direction of the papillary approximation did not affect the tricuspid regurgitation, the direction and extent of the papillary approximation can change the annular shape and right ventricular sphericity, thus allowing for tricuspid valve repair that is adjustable to each patient's unique anatomy.

Example 2

In Vivo Use of Right Ventricular Papillary Muscle Approximation as Treatment for Tricuspid Regurgitation Right ventricular papillary approximation was performed and compared to a tricuspid annuloplasty using in vivo swine chronic model for validation of the results of the ex vivo example described above.

Figure 25A:
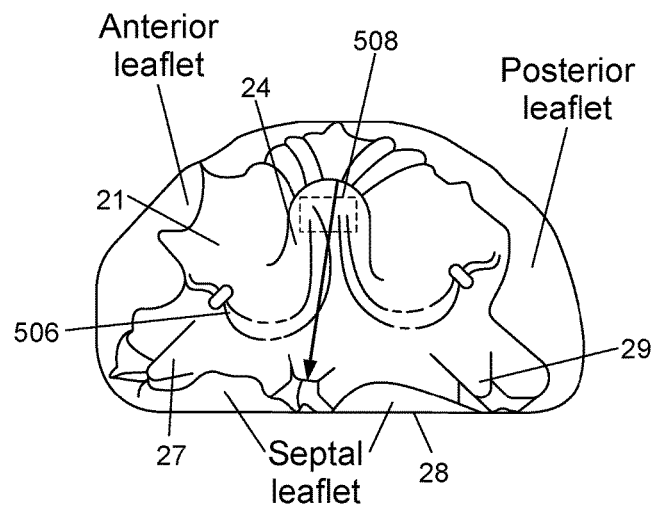
FIG. 25A is a diagram of the in vivo approach to right ventricular papillary approximation.

Tricuspid regurgitation was created in swines (n=5, 50.0±1.3 kg) with beating hearts by annular incisions using a cardioport video-assisted imaging system through thoracotomy. Four to five weeks after the creation of the tricuspid regurgitation, the swines underwent right ventricular papillary approximation or tricuspid annuloplasty on cardiopulmonary bypass via midsternal incision. As shown in FIG. 25A, the anterior papillary muscle 24 of the right ventricle 21 was approximated to the ventricular septum 28 with sutures 506 with pledgets 508. The direction of papillary approximation was A-S1 (i.e., anterior papillary muscle 24 to the midpoint of the medial and posterior papillary muscles) or A-S2 (i.e., anterior papillary muscle 24 to the intersection of the septum 28 and its perpendicular line over the anterior papillary muscle 24). For tricuspid annuloplasty, a rigid ring was implanted as a control. At four weeks after right ventricular papillary approximation or tricuspid annuloplasty, euthanasia was performed.

Figure 25B:
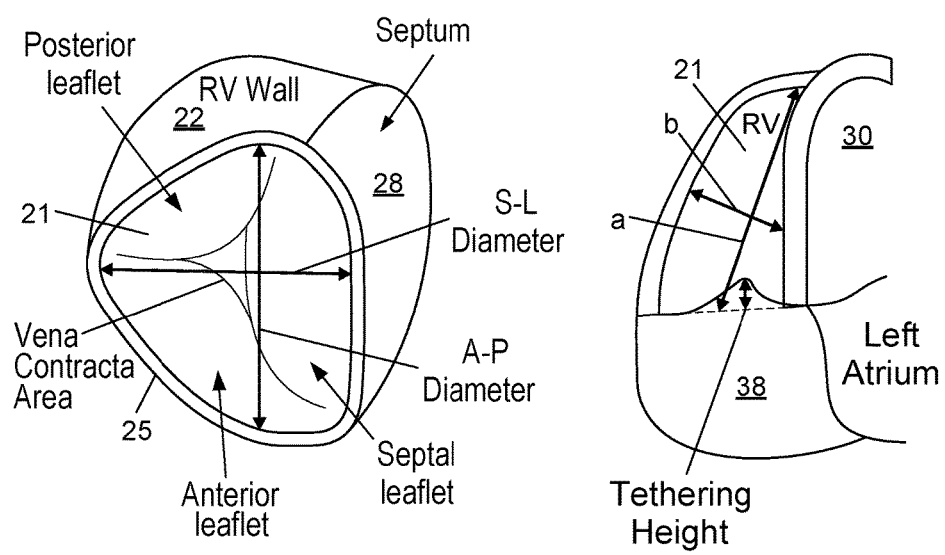
FIG. 25B is a diagram of various cardiac dimensions.

Color-Doppler and 3-dimensional epicardial echocardiography were obtained before creation tricuspid regurgitation, before and after right ventricular papillary approximation or tricuspid annuloplasty, and at euthanasia. Tricuspid regurgitation volume per beat was calculated from the effective regurgitant orifice area (using the flow convergence method) and the velocity-time integral of tricuspid regurgitation. Referring to FIG. 25B, tricuspid annular dimensions, RVSI, and tricuspid valve tethering height were also measured by three-dimensional echocardiography.

Figure 28A:
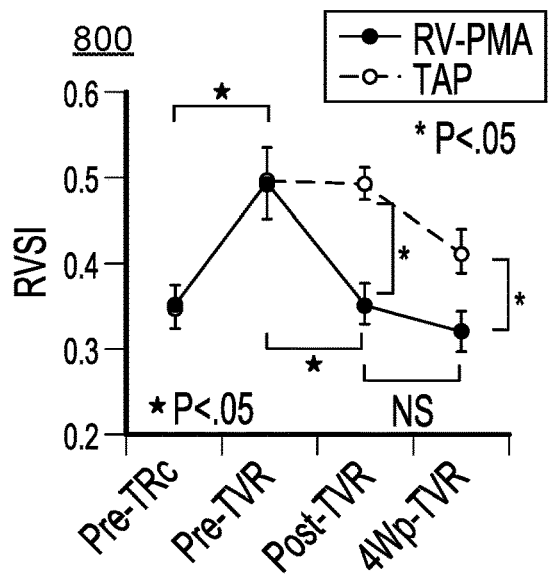
FIGS. 28A and 28B are graphs of RVSI and tethering height, respectively, versus time.
Figure 28B:
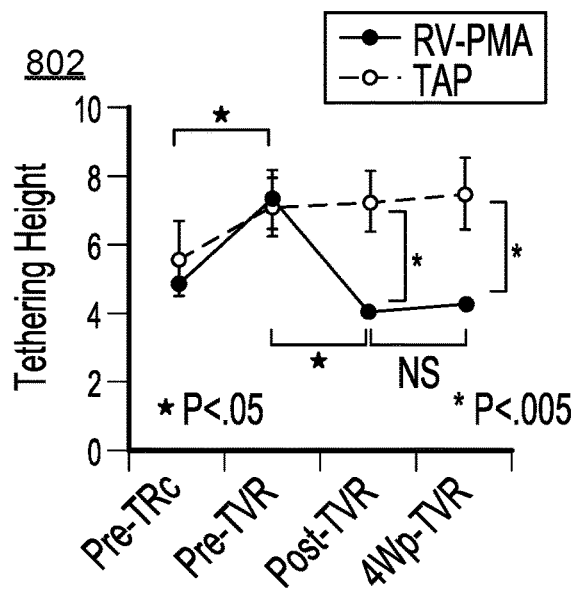

Right ventricular papillary approximation reduced the tricuspid regurgitation grade from moderate-severe to mild. Referring to FIGS. 26A and 26B, right ventricular papillary approximation reduced the tricuspid regurgitation volume (graph 600) and the vena contracta area of tricuspid regurgitation (graph 602) as effectively as tricuspid annuloplasty. The effect of right ventricular papillary approximation persisted after four weeks. Referring to FIGS. 27A and 27B, right ventricular papillary approximation also significantly reduced the tricuspid annular area (graph 700) by reducing its septal-lateral diameter (graph 702), by approximately the same extent as tricuspid annuloplasty. Right ventricular papillary approximation did not change the anterior-posterior annular diameter. The annulus was slightly dilated after four weeks although only the septal-lateral diameter showed any statistical significance (graph 702). Referring to FIGS. 28A and 28B, right ventricular papillary approximation also reduced RVSI (graph 800) and tricuspid valve tethering height (graph 802). Tricuspid annuloplasty minimally reduced RVSI only after four weeks (graph 800) but did not change the tethering height significantly (graph 802). No suture detachment or tricuspid stenosis was observed after right ventricular papillary approximation.

These in vivo experiments demonstrate that right ventricular papillary approximation can alleviate functional tricuspid regurgitation by reducing annular dimension, RVSI, and valve tethering in a chronic tricuspid regurgitation animal model.

Example 3

Force Tolerated by Fixation Mechanism

Figure 29A:
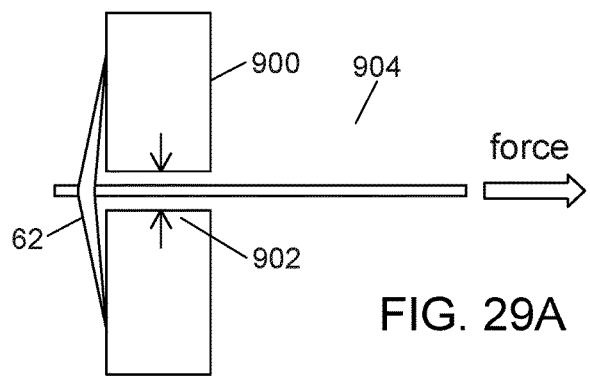
FIG. 29A is a diagram of an experiment to determine the force tolerance of an umbrella fixation mechanism.

An experiment was conducted to evaluate the amount of force a two-membrane umbrella (e.g., umbrella 62) can tolerate. Referring to FIG. 29A, a hole 902 was made through fresh myocardium 900 of ventricular septum and a device 904 including an umbrella 62 at its distal end was introduced into the hole. The size of the hole was changed from 8-16 Fr and the force that the umbrella 62 was able to tolerate (i.e., the force that could be applied before the device detached from the septum) was measured.

Figure 29B:
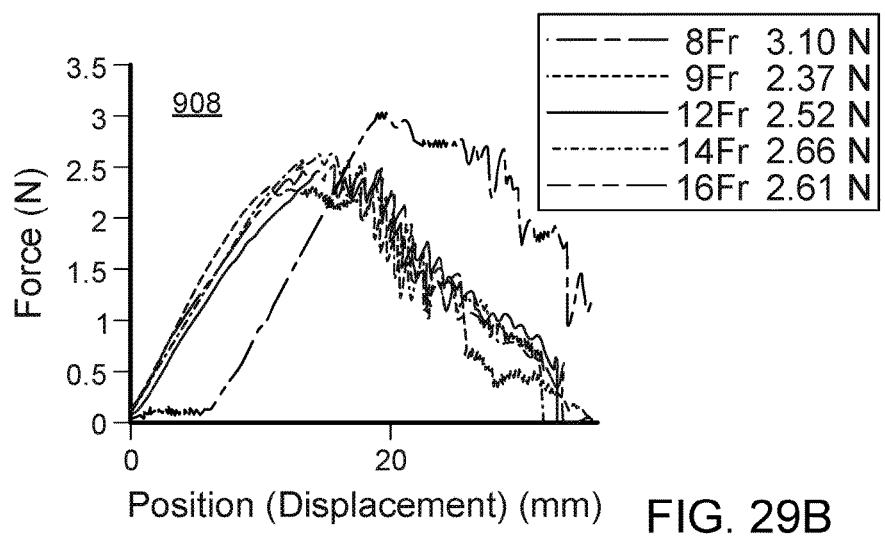
FIG. 29B is a graph of the results of the experiment of FIG. 29A.

The measured force is shown in a graph 908 of FIG. 29B. The forces applied at the umbrella 62 are about 2.5-3 N, regardless of the size of the hole 902. In some cases, a diseased heart, such as a heart with right ventricular failure or pulmonary hypertension, may exert forces greater than 2.5-3 N.

Figure 30:
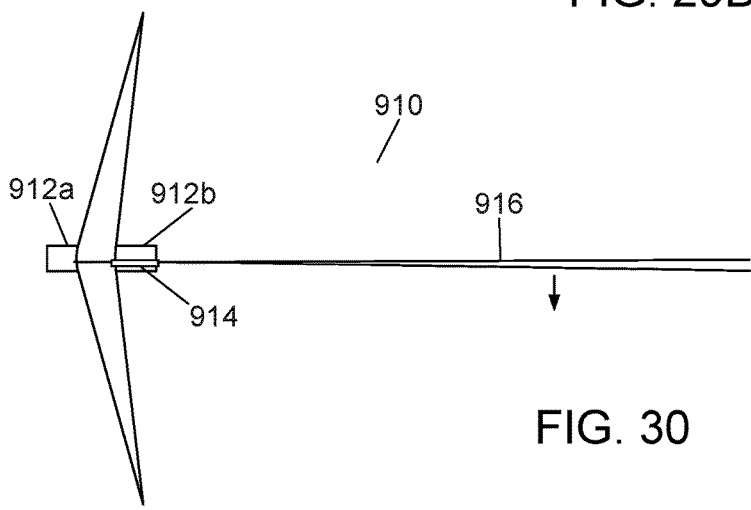
FIG. 30 is a diagram of a reinforced umbrella tip.

Referring to FIG. 30, a reinforced umbrella tip 910 was fabricated to improve its strength. The umbrella tip 910 was anchored with crimping parts 912a, 912b. A small internal tube 914 was set in the crimping part 912b and two small nitinol wires 916 were threaded through the tube 914. The force that can be tolerated by the reinforced tip is increased to 5.94 N.

FIGS. 31A-31C show forces tolerated by other fixation mechanisms. A single nitinol anchor can tolerate 0.71 N (curve 918) and two nitinol anchors can tolerate 1.47 N (curve 920). A 3 mL balloon 48 can tolerate 8.11 N (curve 922). For comparison, the forces tolerated by an umbrella 62 (2.61 N; curve 924) and the reinforced umbrella 910 (5.94 N; curve 926) are also shown.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A device for treating tricuspid regurgitation, the device comprising:
   a shaft;
   a first fixation mechanism disposed on a distal end of the shaft, wherein the first fixation mechanism is configured to anchor the device to a first cardiac tissue, wherein the first fixation mechanism is configured to be folded against the shaft to be substantially parallel to the shaft in a closed configuration, and to be expanded outward from the shaft in an open configuration;
   a second fixation mechanism disposed on a proximal end of the shaft, wherein the second fixation mechanism is configured to anchor the device to a second cardiac tissue, wherein the second fixation mechanism is configured to be folded against the shaft to be substantially parallel to the shaft in a closed configuration, and to be expanded outward from the shaft in an open configuration;
   a locking mechanism to lock the first and second fixation mechanisms in the open configurations, the locking mechanism comprising a first tube arranged around the shaft, a second tube arranged around the first tube, and a spring configured to cause the first tube to close around the shaft to lock the first and second fixation mechanisms in the open configurations; and
   an approximation mechanism connecting the first fixation mechanism and the second fixation mechanism, wherein the approximation mechanism causes the second fixation mechanism to move along the shaft toward the first fixation mechanism to approximate the first cardiac tissue and the second cardiac tissue.

2. The device of claim 1, wherein the approximation mechanism includes at least one of a string, a wire, and a thread.

3. The device of claim 1, wherein the locking mechanism is configured to lock the device in a configuration that causes the first cardiac tissue and the second cardiac tissue to be approximated together.

4. The device of claim 3, wherein the first tube of the locking mechanism comprises a hook to engage a ratchet along the shaft.

5. The device of claim 1, further comprising a sheath configured to contain the shaft, and wherein the first and second fixation mechanism are collapsed to be substantially parallel to the shaft when the shaft is contained within the sheath.

6. The device of claim 1, wherein the first cardiac tissue is at least one of papillary muscle and right ventricular free wall, and the second cardiac tissue is ventricular septal tissue.

7. The device of claim 1, wherein the shaft includes an actuator.

8. The device of claim 1, wherein the approximation mechanism causes the second fixation mechanism to move along the shaft toward the first fixation mechanism such that at least a portion of the shaft is not between the first fixation mechanism and the second fixation mechanism.

9. The device of claim 1, wherein:
   the first fixation mechanism is configured to expand outwardly from the shaft to anchor the device to the first cardiac tissue, and
   the second fixation mechanism is configured to expand outwardly from the shaft to anchor the device to the second cardiac tissue.

10. The device of claim 1, wherein the approximation mechanism is configured to be pulled to cause the second fixation mechanism to move along the shaft toward the first fixation mechanism.

11. The device of claim 1, wherein the shaft comprises a thread, and the first tube comprises a hook configured to be pushed against the thread of the shaft to lock the first and second fixation mechanism in the open configurations.

12. The device of claim 11, wherein the spring is positioned between the hook and the second tube.

13. The device of claim 12, wherein the first tube comprises a proximal end and a distal end, the proximal end of the first tube comprising the hook of the first tube, and the distal end of the first tube being engageable with a control device to decouple the first tube and the shaft.

14. The device of claim 1, wherein:
   the first fixation mechanism comprises first and second hook members, the first and second hook members of the first fixation mechanism extending outwardly from the shaft toward the proximal end of the shaft, and
   the second fixation mechanism comprises first and second hook members, the first and second hook members of the second fixation mechanism extending outwardly from the shaft toward the distal end of the shaft.

* * * * *